(12) United States Patent
Tindle et al.

(10) Patent No.: US 6,183,745 B1
(45) Date of Patent: Feb. 6, 2001

(54) SUBUNIT PAPILLOMA VIRUS VACCINE AND PEPTIDES FOR USE THEREIN

(75) Inventors: Robert Tindle, Kenmore; Germain Fernando, Jamboree Heights; Ian Frazer, St. Lucia, all of (AU)

(73) Assignees: The University of Queensland, Queensland; CSL Limited, Victoria, both of (AU)

(*) Notice: Under 35 U.S.C. 154(b), the term of this patent shall be extended for 0 days.

(21) Appl. No.: 08/075,541
(22) PCT Filed: Sep. 24, 1993
(86) PCT No.: PCT/AU91/00575
  § 371 Date: Jun. 10, 1993
  § 102(e) Date: Jun. 10, 1993
(87) PCT Pub. No.: WO92/10513
  PCT Pub. Date: Jun. 25, 1992

(30) Foreign Application Priority Data

Dec. 12, 1990 (AU) .................................................. 3878
Dec. 12, 1991 (WO) .................................. PCT/AU91/00575

(51) Int. Cl.$^7$ ..................................................... A61K 39/12
(52) U.S. Cl. ...................... 424/185.1; 530/350; 530/395; 530/403
(58) Field of Search ............................ 530/300, 324.33, 530/350, 395, 806; 424/88, 89, 185.1, 184.1, 204.1

(56) References Cited

FOREIGN PATENT DOCUMENTS

| 0 375 555 | 6/1990 | (EP) | C07K/7/08 |
| 0 386 734 | 12/1990 | (EP) | C07K/15/04 |
| 86/05816 | 9/1986 | (WO) | C12Q/1/68 |

OTHER PUBLICATIONS

Bernard, H–U, Trends in Microbiol. 2(4): 140–143 (Apr. 1994), Coevolution of papilloma viruses with human populations.

Crook, T., et al., EMBO J. 8(2): 513–519 (1989), "Continued expression of HPV–16 E7 protein is required for maintainance of the transformed phenotype of cells co–transformed by HPV–16 plus EJ–ras.".

Jenison, S. A., et al., J. Virology 62:2115–2123 (Jun. 1988), "Identification of immunoreactive antigens of human papilloma virus Type 6b by using *Escherichia coli*–expressed fusion proteins".

Kilgus, J., et al., "Analysis of the Permissive Association of a Malaria T Cell Epitope with DR Molecules, "*J. Immunol.,* 146(1):307–15, (Jan. 1, 1991) (Abstract only).

Partidos, C.D., et al., "Immune Responses in Mice Following Immunization with Chimeric Synthetic Peptides Representing B and T Cell Epitopes of Measles Virus Proteins, "*J. Gen. Virol.* 72 (Pt 6): 1293–9, (Jun. 1991) (Abstract only).

Fern, J., et al., "Promiscuous Malaria Peptide Epitope Stimulates CD45Ra T Cells from Peripheral Blood of Non-exposed Donors,"*J. Immunol.* 148(3):907–13, (Feb. 1, 1992) (Abstract only).

Fossum, B., et al., "Overlapping Epitopes Encompassing a Point Mutation (12 GLY—>Arg) in pP21 ras can be Recognised by HLA–DR, –DP and –DQ Restricted T Cells, "*Eur. J. Immunol.* 23(10:2687–91, (Oct. 1993) (Abstract only).

Reece, J.C., et al., "Mapping the Major Human T Helper Epitopes of Tetanus Toxin. The Emerging Picture, "*J. Immunol.* 151(11):6175–84 Dec. 1, 1993) (Abstract only).

Rees, A.D., et al., "The Effect of Lipoylation on DC4 T–Cell Recogniton of the 19,000 MW Mycobacterium Tuberculosis Antigen, "*Immunol.* 80(3):407–14, (Nov. 1993) (Abstract only).

Sharma, P., et al., "Co–Dominant and Reciprocal T–Helper Cell Activity of Epitopic Sequences and Formation of Junctional B–Cell Determinants in Synthetic T:B Chimeric Immunogens, "*Vaccine* 11(3):1321–6, (Oct. 1993) (Abstract only).

Kaumaya, P.T., et al., "Peptide vaccines Incorporation a "Promiscuous "T–Cell Epitope Bypass Certain Haplotye Restricted Immune Responses and Provide Broad Spectrum Immunogenicity, "*J. Mol. Recog.* 6(2):81–94, (Jun. 1993) (Abstract only).

Fridkis–Hareli, M., et al., "Direct Binding of Myelin Basic Protein and Synthetic Copolymer 1 to Class II Major Histocompatibility Complex Molecules on Living Antigen–Presenting Cells—Specificity and Promiscuity, " *Proc. Nat. Acad, Sci. U.S.* 91(11):4872–6, (May, 1994) (Abs. only).

Chin, L.T., et al., "Site–Directed Primary *in vitro* Immunization: Production of HIV–1 Neutralizing Human Monoclonal Antibodies from Lymphocytes Obtained from Seronegative Donors, "*Immunol.* 81(3):428–34, (Mar. 1994) (Abstract only).

Reece, J.C. et al., Scanning for T Helper Epitopes with Human PBMC Using Pools of Short Synthetic Peptides, *J. Immunol. Meth.* 172(2):241–54, (Jun. 4, 1994) (Abstract only).

(List continued on next page.)

*Primary Examiner*—Thomas M. Cunningham
(74) *Attorney, Agent, or Firm*—Akin, Gump, Strauss, Hauer & Feld, L.L.P.

(57) ABSTRACT

The invention relates to a subunit papillomavirus vaccine which is protective against anogenital human Papillomavirus (HPV) infection. Peptides are also provided, which constitute an antigenic component of the vaccine. The peptide includes the sequence DRAHYNI (SEQ ID NO:11) and structural homologues thereof which concern a single amino acid substitution. The peptide is linked directly or indirectly to one or more amino acid sequences which correspond to a B epitope HPV16 and HPV18. The DRAHYNI (SEQ ID NO:11) sequence corresponds to a T helper epitope sequence.

23 Claims, 5 Drawing Sheets

OTHER PUBLICATIONS

Launois, P., et al., "T–Cell–Epitope Mapping of the Major Secreted Mycobacterial Antigen Ag85A in Tuberculosis and Leprosy, "*Infect. & Immun.* 62(9)3679–87, (Sep. 1994) (Abstract only).

A. Partidos et al., 1991, "Immune responses in mice following immunization with chimeric synthetic peptides representing B and T cells epitopes of measles virus proteins,", *Journal of General Virology*, 72, 1293–1299.

Fern and Good, 1992, "Promiscuous malaria peptide epitope stimulates CD45Ra T cells from the peripheral blood of nonexposed donors, "*The Journal of Immunology*, 148, 907–913;

Sharma et al., 1993, "Co–dominant and reciprocal T–helper cell activity of epitopic sequences and formation of junctional B–cell determinants in synthetic T:B chimeric immunogens, " *Vaccine* ,11, 1321–1326;

Hareli et al., 1994, "Direct binding of myelin basic protein and synthetic copolymer 1 to class II major histocompatibility complex molecules on living antigen–presenting cells—specificity and promiscuity, "*Proc. Natl. Acad. Sci.*USA, 91, 4872–4876;

Chin et al., 1994, "Site–directed primary in vitro immunization: production of HIV –1 neutralizing human monoclonal antibodies from lymphocytes obtained from seronegative donors,"*Immunology* , 81, 428–434;

F. Kaumaya et al., 1993, "Peptide Vaccines Incorporating a 'Promiscuous 'T–cell Epitope Bypass Certain Haplotype Restricted Immune Responses and Provide Broad Spectrum Immunogenicity, " *Journal of Molecular Recognition,* 6, 81–94;

Müller et al., 1990 "Identification of seroreactive regions of the human papillomavirus type 16 proteins E4, E6, E7 and L1, " *Journal of General Virology,* 71, 2709–2717; and Roitt, Brostoff & Male, 1993, *Immunology,* Third Edition.

R.W. Tindle et al., The Molecular Specificity of Linear B–Epitopes in the E7 Open Reading Frame Protein of Human Papillomavirus 16 Defined by Monoclonal Antibodies, 162 *Peptide Research,* vol. 3, No.4 (1990), pp. 162–166.

Szumeness, W., et al., "Hepatitis B Vaccine. Demonstration of Efficacy in a Controlled Clinical Trial in a High–Risk Population in the United States, "N. Engl. J. Med. 303(15): 833–841, (Oct. 9, 1980).

Francis, D.P., et al., "The Prevention of Hepatitis B with Vaccine, " *Ann. Intern. Med.*97(3):362–367, (1982).

Hadler, S.C., et al., "Long–Term Immunogenicity and Efficacy of Hepatitis B Vaccine in Homosexual Men, "*N. Engl. J. Med.* 315(4): 209–214, (Jul. 24, 1986).

Feltkamp, M.C.W., et al., "Vaccuination with Cytotoxic T Lymphocyte Epitope–Containing Peptide Protects Against a Tumor Induced by Human Papillomavirus Type 16–Transformed Cells, "*Eur. J. Immunol.* 23:2242–2249, (1993).

Kadish, A.S., et al., "Cell–Mediated Immunen Responses to E7 Peptides of Human Papillomavirus (HPV) Type 16 are Dependent on the HPV Type Infecting the Cervix whereas Serological Reactivity is not Type Specific, "*J. Gen. Virol.*75:2277–2284, (1994).

Müller, M., et al., "Studies of Papillomavirus Capsid Binding and Uptake by Cells from Different Tissues and Species, " *J. Virol.* (submitted).

Qi, Y.M., et al., "Papillomavirus Particles Bind to Epithelial and Other Cells by a Trypsin Sensitive Receptor, "(manuscript in preparation).

Roden, R.B.S., et al., "Interaction of Papillomavirus with the Cell Surface, " *Amer. Soc. Microbiol.,* (pre–print).

Tindle, R.W., et al., "Antibody, T–Cell Help, and T–Cytotoxic Immune Responses to Human Papillomavirus 16 (HPV16) E7 Open Reading Frame Protein Induced in Mice by Immunisation with a 19–Mer Peptide Conjugated to ISCAR Immunocarrier Without Oil–Based Adjuvant, " *J. Gen. Virol.* (submitted).

Panina–Bordignon, P., et al., "Universally Immunogenic T Cells Epitopes: Promiscuous Binding to Human MHC Class II and Promiscuous Recognition by T Cells, "*Eur. J. Immunol.* 19(2): 2237–42, (Dec. 1989) (Abstract only).

Ho, P.C., et al., "Identification of Two Promiscuous T Cell Epitopes from Tetanus Toxin, "*Eur. J. Immunol.* 20(3) :477–83, (Mar. 1990) (Abstract only).

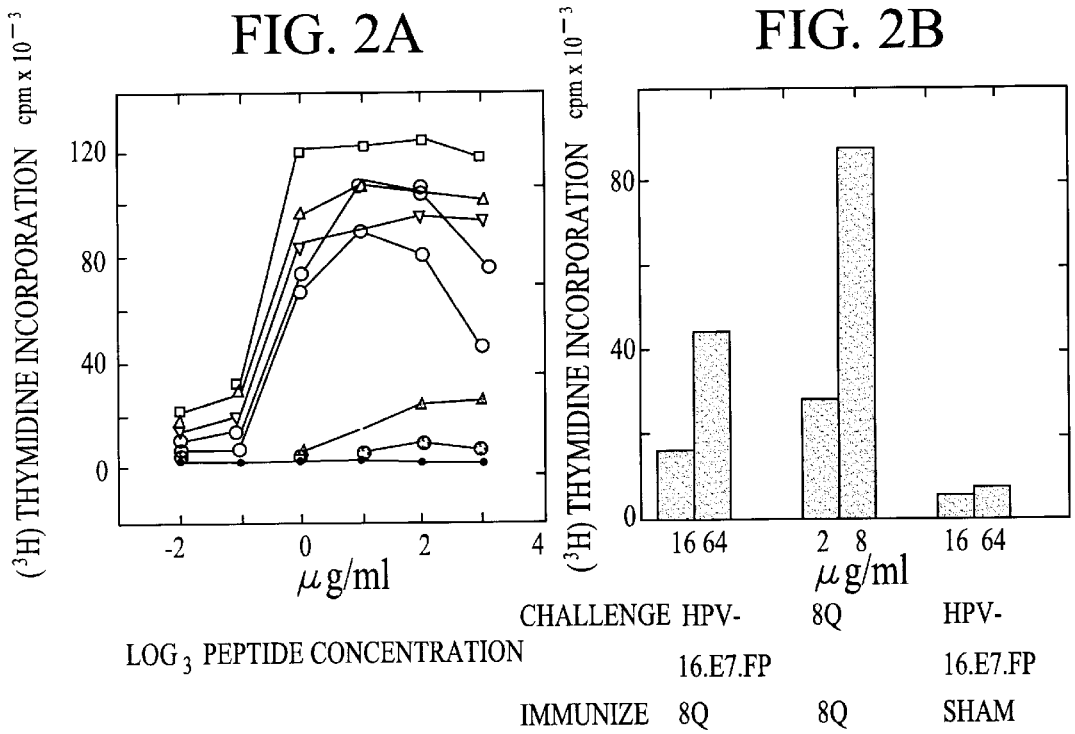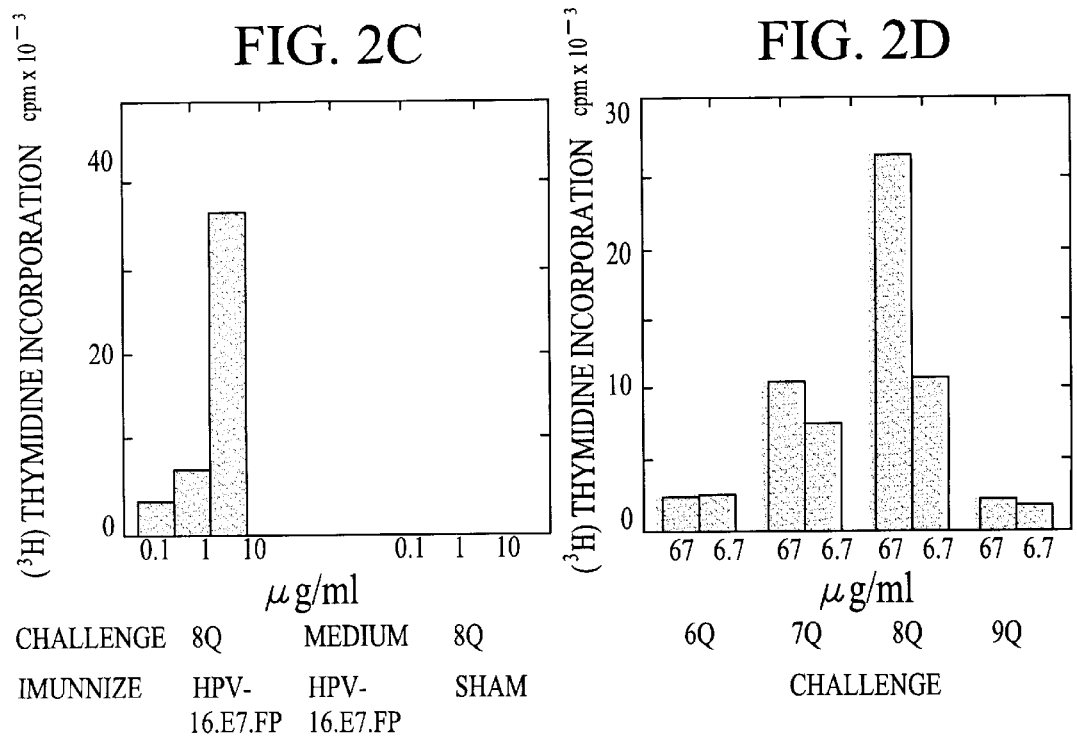

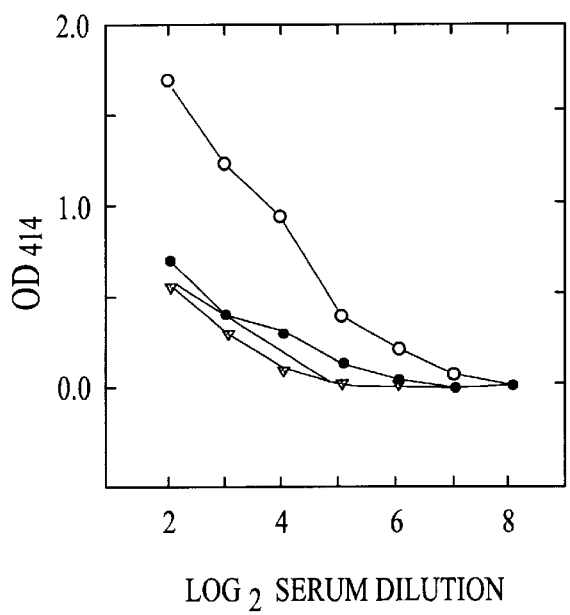 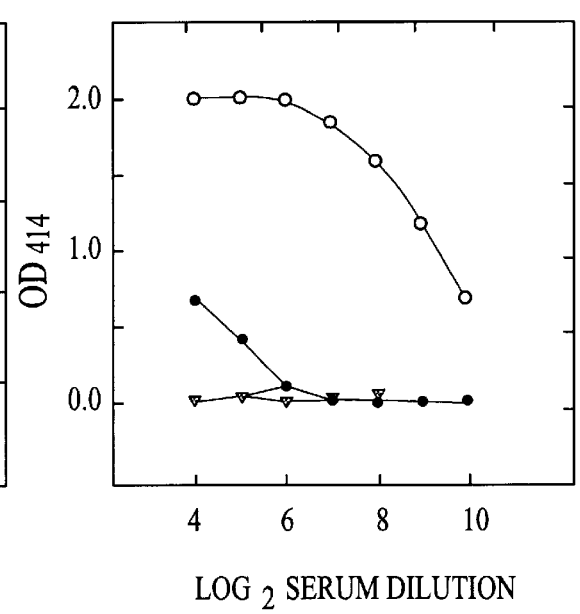
FIG. 3A
FIG. 3B

SUBUNIT PAPILLOMA VIRUS VACCINE AND PEPTIDES FOR USE THEREIN

FIELD OF THE INVENTION

This invention relates to a subunit papillomavirus vaccine which is protective against anogenital human papillomavirus (HPV) infection. The invention also includes within its scope peptides which constitute an antigenic component of the vaccine.

BACKGROUND OF THE INVENTION

It is well known (e.g. in "Papilloma Viruses and Human Cancer" edited by H. Pfister and published by CRC Press Inc. in 1990) that papilloma viruses can be classified into several distinct groups based on the host in which they infect. Human papilloma viruses (HPV) can be further differentiated into types 1–56 depending on DNA sequence homology. Types 16, 18 and 42 are associated with the majority of in situ and invasive carcinomas which may occur in the anogenital tract and in particular the cervix. In this regard, a number of cervical intra epithelial neoplasias and carcinomas of the cervix have been associated with HPV16 and HPV18. (Lancaster et al 1987: Cancer Metast. Rev. 6653 and Pfister 1987. Adv. Cancer Res 48 113). These same two references also point out that papilloma viruses are small DNA viruses encoding up to 8 early and 2 late genes.

The protein from the expression of the early gene E7 varies between 93 to 127 amino acid residues. The E7 protein is the most abundant viral protein in HPV16 containing CaSki and SiHa squamous carcinoma cell lines and in HPV18 containing HeLa and C4-1 lines. (Seedorf et al. 1987. EMBO J. 6, 139). DNA transfection experiments implicate the E6 and E7 ORF proteins in in vitro transformation of mouse fibroblasts (Yasumoto et al. 1986. J. Virol., 57, 572), rat epithelial cells (Matlashewski et al. 1987. EMBO J. 6, 1741) and primary human keratinocytes (Schlegel et al. 1988, EMBO J. 7, 3181; Pirisi et al. 1987. J. Virol. 61, 1061). Cooperation with an active ras oncogene leads to full transformation (Matlashewski et al. 1987. EMBO J. 6, 1741) and there is a requirement for continued expression of the E7 gene to maintain the transformed phenotype (Crook et al. 1989. EMBO J. 8, 513). The E7 protein may be recognised by the immune system, since anti E7 antibodies can be detected in the serum of approximately 20% of patients with HPV16 associated cervical lesions (Jenison et al. 1988. J. Virol. 62, 2115; Jochmus—Kudielka et al. 1989. J. Natl. Cancer Institute 81, 1698; Smillie et al. 1990. Immunol. Infect. Dis. 1, 13).

In addition to types 16, 18 and 42, further genotypes 6, 11, 31, 33, 35 and 39 which fall within the same sub group as types 16, 18 and 42 are infective for anogenital epithelium (Gissman Cancer Surveys 3. 162–181 (1984) Zur Hausen & Schneider The Papillomaviruses p245–263 Edited by Howley and Salzman New York Plenum Press (1987)). The DNAs of HPV types 16 and 18 are frequently found in genital tumours (Durst et al.) J. Gen Virol. 66 1515–1522 (1985), Gissman et al PNAS 80, 560–563 (1983)) supporting the concept that members of this sub group have an essential role in the etiology of genital cancer (Syrjanen et al British Journal of Obstetrics and Gynaecology 92 1086–1092 (1985)). Integration of HPV16 DNA into host genomes is frequently observed in cervical cancers with interruption of the E2 viral ORF, the protein product of which region transregulates early ORF transcription from the p97 promoter and retention of intact E6 and E7 ORFs.

Abundant circumstantial evidence implicates host immune mechanisms in the control of HPV associated tumours of the anogenital epithelium (Singer et al British Medical Journal 288, 735–736 1984). There is an increased incidence of pre-neoplastic (Frazer et al Lancet ii 657–660 1986) and neoplastic associated lesions in homosexual men immunosuppressed by human immunodeficiency virus infection and a markedly increased risk of squamous cell carcinoma (SCC) of the cervix and vulva but not of control organs such as breast and rectum in immunosuppressed allograft recipients (Sheil and Flavel Ninth Report of Australian and New Zealand Combined Dialysis and Transplant Registry pp 104–112 Edited by APS Disney 1986).

Taken with the above, the normal natural history of HPV infection in most patients with alpha-gamma globulinemia suggests that cellular rather than humoral responses are important for the control of the phenotypic expression of HPV infection (Kirschner Progress in Medical Virology 1986).

Standard immunological approaches to the study of anogenital HPV infection have been hampered by the lack of a suitable animal model and of an in vitro epithelial cell culture permissive for HPV.

Vaccines have also been proposed in regard to HPV with however only indifferent success.

It has been proposed to use vaccines containing autogenous tumor homogenates (Abcarian et al J. Surg Res 22: 231–236 (1977) Dis Colon Rectum 25:64851 1982 Dis Colon Rectum 19: 237–244 (1976)). However it has recently been advocated that patients should no longer be treated with autogenous vaccines because of the potential oncogenic effect of the viral DNA (Bunney 1986 Br Med J 293 1045–1047).

In relation to production of genetically engineered vaccines this matter has been discussed in Pfister (1990) above and it seems that difficulty has been experienced in obtaining an effective vaccine because of the plethora of different papilloma virus types. Pfister however points out that attention should be directed to the so called early proteins (ie. E1, E2, E3, E4, E5, E6, E7 or E8) because these proteins are most likely synthesised in the proliferating basal cells of a wart infection in contrast to the structural proteins which are expressed in the upper epidermal layers. Therefore according to Pfister (1990) virus capsid protein appears to be limited in relation to use in a vaccine. The use of recombinant vaccinia viruses in in vitro test systems for papilloma virus early proteins in eukaryotic cells has been discussed also in Pfister (1990). This may take the form of a live vaccine consisting of genetically modified vaccinia virus expressing papilloma virus proteins or on the surface of paraformaldehyde fixed autologous cells infected in vitro with vaccinia recombinants or transfected with other expression vectors. Another strategy for vaccine development as discussed in Pfister (1990) is to use an immune stimulating complex of the glycoside Data on successful prophylactic vaccination exist only for bovine fibropapillomas homogenised homogenate of bovine fibropapillomas and has been shown to provide limited immunity (Olson et al. J am Vet Med Assoc 135, 499 (1959) Cancer Res 22 463 (1962)). A vaccine including an engineered L1 fusion protein (Pilacinski et al. UCLA Symp. Molecular and Cellular Biology New Series Vol 32 Papilloma Viruses Molecular and Clinical Aspects Alan R Liss New York 1985 257) has also been used in calves but proved unsuccessful in humans. In Pfister (1990) it is stated that there is presently no evidence for a possible prevention of HPV infection by the use of a capsid protein vaccine, but induction of an antitumor cell immunity appears to be feasible.

The L1 and L2 genes have been the basis of vaccines for the prevention and treatment of papilloma virus infections and immunogens used in the diagnosis and detection of papilloma viruses (International Patent Specifications W08605816 and E08303623). However, it appears that no commercial usage of these vaccines have taken place.

Reference may also be made to Patent Specification EP386734 which describes new immunogenic regions of HPV16 E7 protein which may be useful in vaccines, EP 375555 which describes HPV16 peptides useful as immunoassay reagents for the detection of HPV16 proteins and which contain an antigenic determinant for HPV16, a reference in VACCINE (1990) 8 3, 199–204 which describes vaccines including recombinants expressing HPV E5, E6 or E7 ORF intended for use in providing antitumor activity, Australian Specification 52860/90 which describes screening antibodies for specificity to an antigen which is an epitope of HPV16 L1 or E7 proteins, Australian Specification 75535/87 which describes synthetic peptides of HPV corresponding to an amino acid sequence region having at least one reverse turn and predicted hydrophilicity, Patent Specification EP217919 which describes type specific papillomavirus DNA sequences and peptides useful in vaccines containing 15–75 nucleotides, U.S. Pat. No. 4,551,270 which describes at least one antigenic determinant of papillomavirus and immunogens and vaccines containing the antigenic determinant, Patent Specification EP412762 which describes a polypeptide having the sequence Leu-Tyr-Cys-Tyr-Glu-Gln-Leu-Asn-Asp-Ser-Ser (SEQ ID NO:51) which inhibits binding of the HPV E7 protein to retinoblastoma gene which may be used in vaccines for treatment of cervical cancer and genital warts, French Specification 2643817 which describes a vaccine for treatment of tumours induced by papillomavirus containing recombinant poxvirus with heterologous DNA encoding region of non structural papillomavirus, Japanese Specification J01061665 which describes an antibody formed to an antigen polypeptide of HPV16 E6 or E7 protein which antigen polypeptide is Tyr-Gln-Asp-Pro-Gln-Glu-Arg-Pro-Arg-Lys-Leu-Pro-Gln-Leu-Cys (SEQ ID NO:52) which is part of E6 protein or Cys-Tyr-Gln-Leu-Asn-Asp-Ser-Ser-Glu-Glu-Asp-Glu-Ile-Asp (SEQ ID NO:53) which is part of E7 protein, Australian Specification 76018/87 which describes expression products of HPV16 or HPV18 which may be used for the production of antibodies, EP235187 which describes kits containing polypeptide(s) expressed by several groups of papilloma virus including HPV16 and HPV18 which are expression products of E6, E7 or L2 genes and U.S. Pat. No. 4,777,239 which includes, diagnostic synthetic peptides for HPV one of which includes residues 45–58 of protein E6 and 40–50 of protein E7 which may be used as a therapeutic agent.

Of particular interest in the prior art discussed above is specification EP375555 which describes a peptide AEPDRAHYNIVTFC (SEQ ID NO:56) which may be used as an immunoassay reagent for diagnosis of HPV16 antibodies. This peptide includes the DRAHYNI (SEQ ID NO:11) sequence. However it is clear from a review of this document that there was no realisation that the DRAHYNI (SEQ ID NO:11) sequence corresponded to a T helper cell epitope of the ORF of E7 protein of HPV16 and the consequences in regard to HPV therapy as discussed in this patent specification.

Of particular relevance also is specification EP386734 which discloses a number of peptides, one of which (i.e., No. (V)) comprises the sequence Asp-Glu-Ile-Asp-Gly-Pro-Ala-Gly-Gln-Ala-Glu-Pro-Asp-Arg-Ala-His-Tyr (SEQ ID NO:54). It will be noted that this sequence includes the sequence DRAHY (SEQ ID NO:55). While this particular peptide is described as corresponding to a useful immunogenic region of HPV16 E7 protein, and thus useful in vaccines, it will be appreciated from the discussions hereinafter that the sequence DRAHYNI (SEQ ID NO:11) has a more useful antigenic property and thus will stimulate a far greater immune response.

SUMMARY OF THE INVENTION

In this specification amino acids are represented by single letter codes as follows:

| | | | |
|---|---|---|---|
| Phe: F | Leu: L | Ile: I | Met: M |
| Val: V | Ser: S | Pro: P | Thr: T |
| Ala: A | Tyr: Y | His: H | Gln: Q |
| Asn: N | Lys: K | Asp: D | Glu: E |
| Sys: C | Trp: W | Arg: R | Gly: G |

It is therefore an object of the invention to provide a vaccine including an antigenic component which may be utilised to treat HPV infections and which also may be used to provide immunity against HPV infection.

BRIEF DESCRIPTION OF THE DRAWINGS

The foregoing summary, as well as the following detailed description of preferred embodiments of the invention, will be better understood when read in conjunction with the appended drawings.

FIG. 1 comprises an amino acid sequence shown in FIG. 1A and three bar charts shown in FIG. 1B.

FIG. 2 shows the in vitro proliferative response (panels A–C) and lymphokine production (panel D) of LNC from mice immunised 8 days previously with HPV16 E7 or E7 peptides, and challenged with HPV16 E7 or various E7 peptides.

FIG. 3 shows plots of log$_2$ serum dilution versus OD$_{414}$ for immunisation with peptide 8Q (SEQ ID NO:3) primed mice for in vivo challenge with HPV16 E7 produced from a recombinant vaccinia virus. For clarity, only ELISA results on pooled 8 day sera from 8Q (SEQ ID NO:3) primed mice and 'sham' primed mice challenged with VAC-E7 or WR-VAC on (panel A) HPV16 E7 FP, or (panel B) peptide 8Q (SEQ ID NO:3) are shown.

DETAILED DESCRIPTION OF THE PREFERRED EMBODIMENTS

Figure 1A:
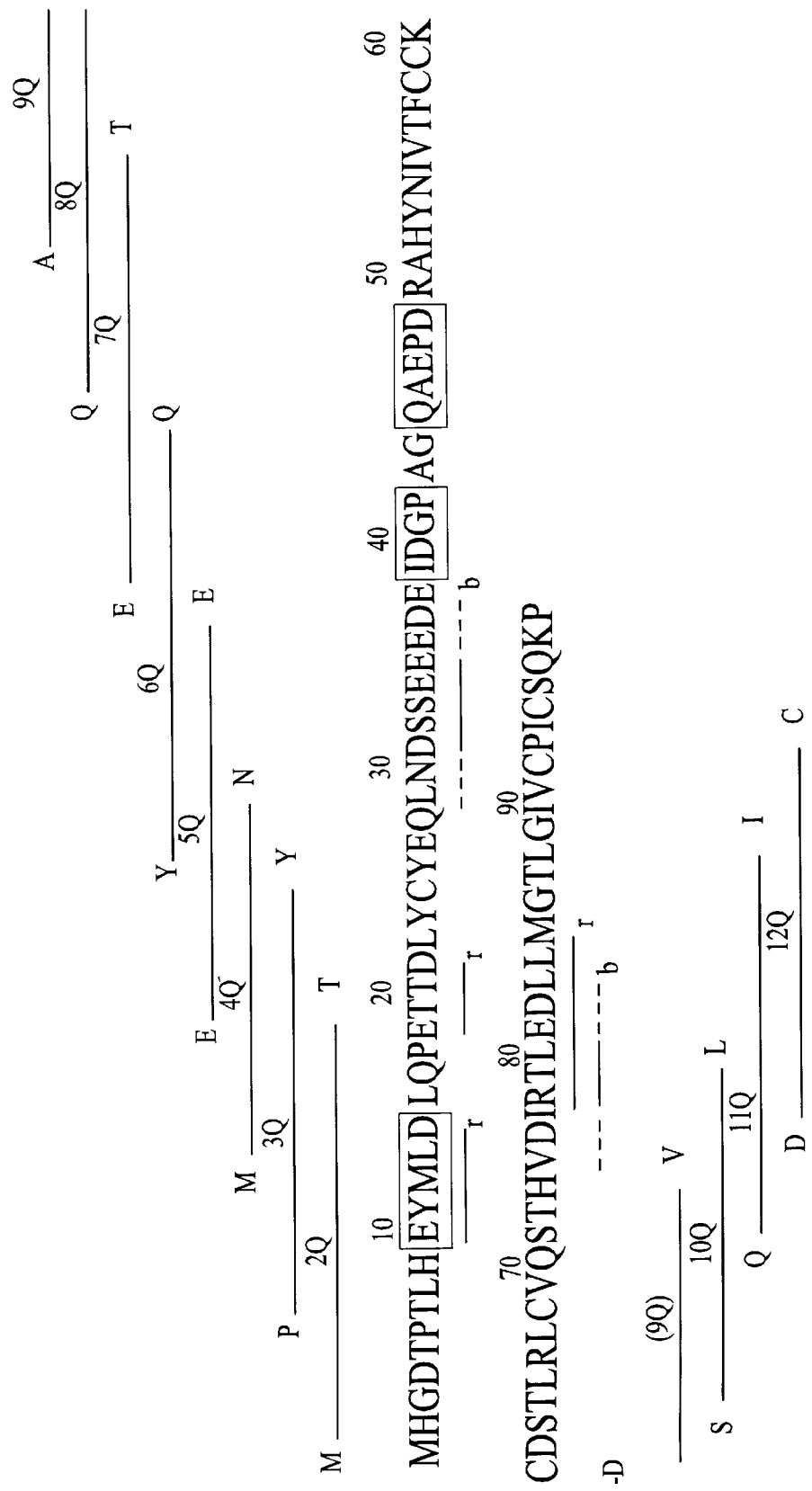
FIG. 1A shows a set of overlapping peptides (termed 2Q, 3Q, 4Q, 5Q, 6Q, 7Q, 8Q, 9Q, 10Q, 11Q and 12Q, SEQ ID NOS:43, 44, 45, 36, 31, 5, 3, 47, 48, 49 and 50, respectively) spanning the putative HPV16 E7 protein, used to locate the position of T-proliferative epitopes. Linear B-epitopes defined by monoclonal antibodies 8F, 4F and 10F (see Tindle et al., *J. Gen. Virol.* (1990), 71, 1347–1354) are boxed. Underlining denotes the position of putative T-epitopes as predicted by the Rothbard (r) and DeLisi and Berzofsky (b) algorithms, respectively.

The peptides utilised as the antigenic component in the HPV vaccine of the invention have the structure DRAHYNI (SEQ ID NO:11), which peptide is linked directly or indirectly to one or more amino acid sequences which correspond to a B epitope of HPV16 or HPV18.

Suitable B epitopes may be selected from HPV16 E7 epitopes which include QAEPD (SEQ ID NO:12), IDGP (SEQ ID NO:13), EYMLD (SEQ ID NO:14) and YMLD (SEQ ID NO:15). Suitable B epitopes that may be selected from the HPV18 E7 epitopes include DEIDGVNHQHL (SEQ ID NO: 16) and SEENED (SEQ ID NO:17).

Representative peptides which fall within the scope of the invention include the following:

$B_1$-$A_1$-DRAHYNI (SEQ ID NO:11)-$A_2$     (1)

$B_2$-DRAHYNI (SEQ ID NO:11)-$B_3$     (2)

$B_1$-$A_1$-DRAHYNI (SEQ ID NO:11)-$A_2$-$B_4$     (3)

$B_2$-DRAHYNI (SEQ ID NO:11)-$A_2$     (4)

$A_1$-DRAHYNI (SEQ ID NO:11)-$B_3$     (5)

$A_1$-DRAHYNI (SEQ ID NO:11)-$A_2$-$B_4$     (6)

$B_1$-$A_1$-$B_4$-$A_1$-DRAHYNI (SEQ ID NO:11)-$A_2$     (7)

$B_1$-$A_1$-$B_2$-DRAHYNI (SEQ ID NO:11)-$B_3$-$A_2$-$B_4$     (8)

$B_1$-$A_1$-$B_4$-$A_1$-$B_2$-DRAHYNI (SEQ ID NO:11)-$A_2$     (9)

In the above formulae (1) through (9), $B_1$ and $B_4$ represent B epitope sequences that may be linked to the T epitope sequence indirectly through intervening sequences of amino acids that are not B epitope sequences, such as $A_1$ and $A_2$, which may be the same or different each time present in a formula.

In some cases the B epitope sequence may be linked directly to the T helper epitope sequence as indicated by $B_2$ and $B_3$, which may be the same or different. In such a case, in a first situation, the terminal amino acid of the B helper epitope sequence and the first amino acid of the T epitope sequence may be merged. In other cases, in a second situation the last amino acid of the T helper epitope sequence and the first amino acid of the B epitope sequence may also be merged. In this embodiment therefore $B_2$ represents a B epitope sequence which may include the first situation, and $B_3$ represents a B epitope sequence that may include the second situation. Examples of the first and second situations are

QAEPDRAHYNI (SEQ ID NO:1)-$A_2$     (10)

and $A_1$-DRAHYNIDGP (SEQ ID NO:2)     (11)

In formula (10) the amino acid D which corresponds to aspartic acid represents the first situation and in formula (11) the amino acid I which corresponds to isoleucine represents the second situation.

An especially preferred peptide that may be used in the invention is the peptide QAEPDRAHYNI (SEQ ID NO:1)-$A_2$.

The sequence DRAHYNI (SEQ ID NO:11) in accordance with the present invention has been identified as corresponding to a major T helper cell epitope in the E7 open reading frame (ORF) of HPV16 and HPV18. DRAHYNI (SEQ ID NO:11) corresponds to amino acids 48–54 of the E7 ORF.

The above mentioned peptides which may be utilised in the HPV vaccine of the invention, which may be formed synthetically, may form immunogens capable of eliciting strong antibody response to HPV16 or HPV18 E7 challenge. The T epitope may facilitate the production of antibody to several B epitopes simultaneously.

The HPV vaccine of the invention may also include a suitable adjuvant. For animals infected with HPV suitable adjuvants may be selected from Freunds Complete Adjuvant, Freunds Incomplete Adjuvant, QuilA and saponins generally. In relation to humans it is preferred to utilise an adjuvant which is compatible with humans and an appropriate adjuvant in this regard is ISCOMS (i.e. immunostimulating complexes).

The invention is significant because of its therapeutic value in relation to cervical cancer which like AIDS has a devastating effect on human lives. If a vaccine against these diseases could be developed, it is to the greatest benefit of mankind. Immunisation with attenuated or killed viruses may have inherent risks associated with it. To reduce the risk one could use small peptides containing the necessary B and T epitopes as vaccines. The major advantages of peptide vaccines are (i) feasibility to obtain large quantities of relatively pure peptides by automated chemical synthesis, (ii) the ability to tailor the peptide in such a way that the useful B epitopes could be incorporated into the vaccine construct while deleterious B epitopes could be left out, (iii) if necessary many artificial T-helper epitopes could be incorporated in a mixed vaccine to help overcome MHC restriction in an out bred population.

It is easy to induce antibodies against peptides using Freund's adjuvant in animals provided the peptide concerned has a T-helper incorporated into its sequence. However one has to be able to use an adjuvant less harmful than Freund's, but with equal efficacy when used on humans. Also ideally the adjuvant should be able to elicit CD8+ MHC class I restricted cytotoxic T lymphocytes, when using peptides as immunogens. Immunostimulating complexes (ISCOMS) have the potential of satisfying both the above conditions. ISCOMS are stable molecular structures, with a mean diameter of 35 nm, in which protein antigens are incorporated into a matrix of cholesterol and an adjuvant glycoside QuilA.

In order to incorporate a protein into ISCOMS the protein has to have a lipid binding region. Recently non lipid binding proteins were bound to ISCOMS by exposing hidden lipid binding regions of the proteins by changing the pH or by coupling with a protein known to bind lipids. In these studies the researchers have used the whole length proteins which may not be safe to use on humans and/or which are hard to prepare to purity necessary for human use. In this specification a method is described hereinafter of preparing vaccines using small synthetic peptides of defined B and T cell epitopes coupled to a synthetic lipid binding peptide, in mice. Since many peptides do not bind lipids on their own they could be made lipid binding by coupling to the lipid binding peptide LAP20 which takes an amphiphatic α-helical confirmation in the presence of lipid.

Materials and Methods

Synthetic Peptides

Peptides were synthesised using the simultaneous multiple peptide technique originally described by Houghten (PNAS U.S.A. 82 5131–5135 1985) employing derivatised t-Boc amino acids on benzhydryl resin, or using Fmoc chemistry on an Applied Biosystems 431 A Peptide Synthesiser. Peptides were routinely analysed for homogeneity by HPLC. Peptides less than 90% pure were purified. The amino acid composition of all peptides was checked, and peptide 8Q (SEQ ID NO:3) was amino acid sequenced. Data were confirmed using 2 or 3 separate syntheses of peptides and two different chemistries (Fmoc and t-Boc) to preclude batch idiosyncrasy. All peptides were tested for non-specific mitogenicity on unprimed lymph node cells and for toxicity on tuberculin PPD-primed T-cells. Stock solutions were made by dissolving peptides in tissue culture medium at 5 mg per ml. In some cases acetic acid to 5% was added to attain solution.

HPV16 E7 Protein

HPV16 E7 protein was produced as MS2 fusion protein (FP) from a heat inducible phage promoter in a pPLc 24 expression vector (provided by L. Gissmann) in *E. coli* 600/537. FP was partly purified from lysozyme-disrupted bacteria by Triton-X 100 and sequential urea extraction as described (Seedorf et al 1987 EMBO J., 6, 139–144). Purification was monitored on PHAST (Pharmacia) SDS-PAGE. Preparations containing 60–90% pure FP as judged by appropriately sized major bands on gels, were obtained as 8–10 M urea extracts.

Lymph Node Cell (LNC) Proliferation Assays

Mice were immunised subcutaneously in the base of the tail with 20–50 µg of peptide emulsified in complete Freunds adjuvant (H37 Ra.CFA Difco Labs. Detroit). Eight to ten days later mice were killed, ingurinal and periaortic nodes were removed and a suspension of lymph node cells prepared. Cells were plated in triplicate at $4 \times 10^5/0.2$ ml in flat bottomed 96 well microtitre plates in Hepes buffered RPMI 1640 medium containing glutamine, pyruvate, 2% heat inactivated mouse serum and $5 \times 10^{-5}$ M 2-mercaptoethanol, and antigen at various concentrations. After 4 days, cells were pulsed with 1 µCi of ($^3$H)-thymidine (5 Ci/mmol, Amersham, U.K.) and after a further 18 hours, incorporated $^3$H was quantified by B-emission spectroscopy.

Mice

In-bred mouse strains were obtained from University of Queensland animal breeding facility or from Animal Resources Inc. Perth, Western Australia. Mice were used at 8–24 weeks old.

Assay For Cytokine Production

The lymphokine (interleukin-2 (IL-2) and interleukin-4) dependent HT-2 cell line was maintained in vitro in RPMI medium supplemented with 10% fetal bovine serum and 10% supernatant from the IL-2 producing cell line MLA 144. Omission of MLA supernatant resulted in cessation of cell division within 18 hours, as measured by ($^3$H)-thymidine incorporation. Supernatants from LNC proliferation assays were harvested at 3 days and tested for induction of proliferation of HT-2 cells (Ertl et al (1989) J. Virol. 63, 2885–2892) which had been starved of MLA supernatant overnight and washed extensively in serum free medium. $2 \times 10^3$ HT-2 cells in 100 µl RPMI medium supplemented with 10% FCS were cultured in triplicate with 50 µl of LNC proliferation assay supernatant, which had been centrifuged to remove residual lymph node cells. Proliferation was measured 40–48 hours later by a 6 hour ($^3$H)-thymidine pulse (0.5 µCi per well).

Peptide ELISA Assay

Peptides 3Q (SEQ ID NO:44), 6Q (SEQ ID NO:31), 7Q (SEQ ID NO:5) and 8Q (SEQ ID NO:3) were conjugated to bovine serum albumin (BSA) using a single step glutaraldehyde method as described (Avrameus 1969-Immuno Chemistry 6, 43–47). Peptide-BSA conjugates were bound to microtitre plates by incubation at 50 µg/ml in bicarbonate binding buffer pH 9.6. Remaining binding sites on the microtitre plates were blocked with phosphate buffered saline (PBS) containing 5% BSA prior to incubation with serum from mice immunised with various peptide constructs, at a range of dilutions in PBS containing 5% non-fat milk powder, 0.1% BSA, 0.1% Tween20. After appropriate washings, horseradish peroxidase conjugated anti-mouse Ig. (Silenus Laboratories, Australia) and 2,2'-azinobis(3-ethyl-benzthiazoline sulfonate) (ABTS) substrate were added. Optical density (O.D.) was quantified on a Titertek multiscan microtitre plate reader (Flow Laboratories, Scotland) at 414 nm. HPV16 E7/MS FP ELISA assays were conducted with modifications as described (Tindle et al 1990 J. Gen Virol 71, 1347–1354). All ELISA assay plates contained wells which were concurrently incubated with a panel of monoclonal antibodies 8F, 4F and 6D, specific for HPV16 E7 linear epitopes EYMLD (SEQ ID NO:14), IDGP (SEQ ID NO:13) and QAEPD (SEQ ID NO:12) respectively (Tindle et al (1990) Peptide Res. 3, 162–166), as positive and negative controls.

Peptide Immunisation For Antibody Production

Mice were immunised 3 times intraperitoneally (ip.) with 20–50 µg of peptide emulsified in complete Freund's adjuvant at 14 day intervals. Mice were bled from the retro-orbital plexus 8 days after the last injection, serum prepared, and ELISA was performed.

Carrier Priming Assay

Mice (3–5 per group) were immunised ip. with 20–50 µg. of peptide 8Q (SEQ ID NO:3) or PBS emulsified in CFA. Three to five weeks later, mice were infected by tail base scarifaction with $10^7$ plaque forming units (pfu) of recombinant vaccinia virus containing the entire HPV16 E7 gene (VAC-E7) (Drs. A. Minson and J. Sterling, pers. cons.) or $10^7$ pfu of wild-type vaccinia virus (WR-VAC). 7–8 days later, serum was prepared from each mouse, and anti-E7 antibodies were determined by ELISA assay against peptide 8Q (SEQ ID No. 3) or HPV16 E7 FP bound to microtitre plates. Negative controls were mice immunised with irrelevant peptide (6Q) (SEQ ID NO:31), and microtitre plates to which irrelevant peptides were bound.

Results

Lymph Node Cell Proliferation Assays

Figure 1B:
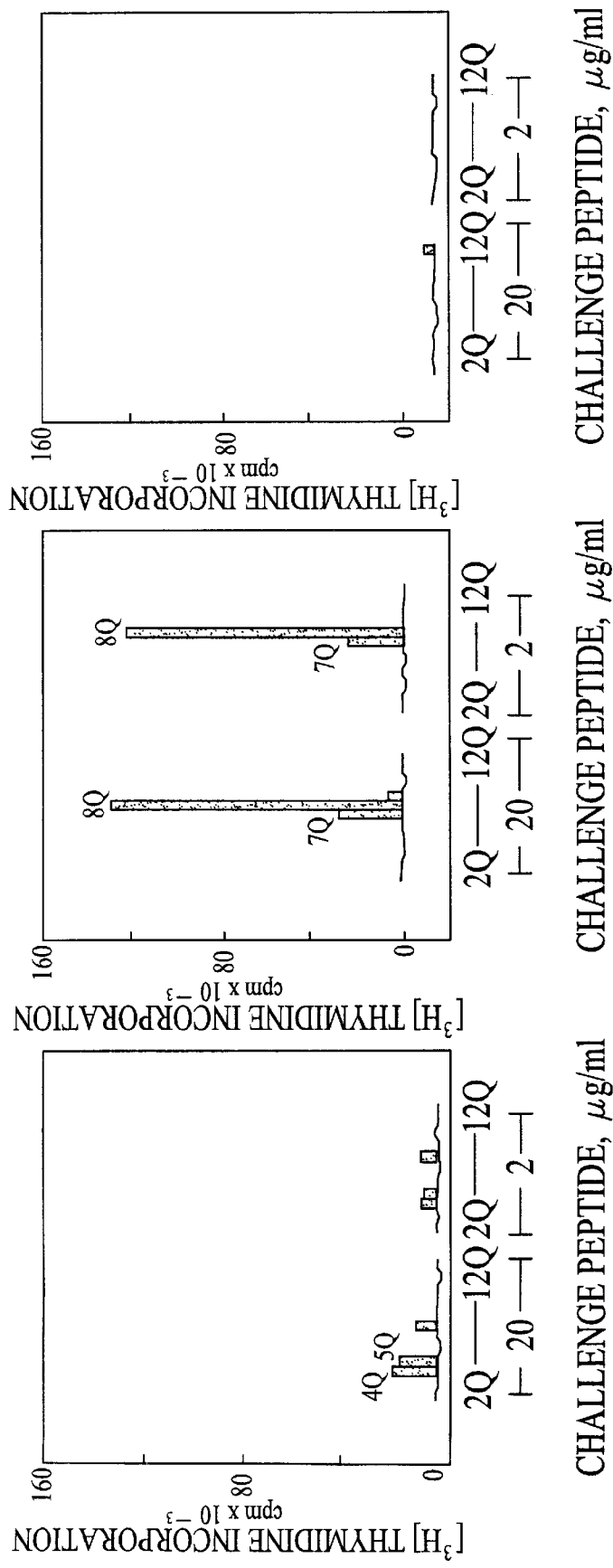
FIG. 1B shows three bar charts, in panels "a", "b" and "c", that illustrate the results obtained by the Lymph Node Cell (LNC) proliferation assay. LNC from C57B1/6 mice immunised with equimolar mixes in CFA of peptides 2Q–5Q (SEQ ID NOS:43,44,45,36, see panel "a"), peptides 6Q–9Q (SEQ ID NOS:31, 5, 3, 47, see panel "b") and peptides 10Q–12Q (SEQ ID NOS:48, 49, 50, see panel "c") were challenged in vitro with 20 μg/mL or 2 μg/mL of individual peptides 2Q–12Q (SEQ ID NOS:43, 44, 45, 36, 31, 5, 3, 47, 48, 49, 50).

A set of overlapping 15–20 mer peptides covering the entire predicted HPV16 E7 protein (FIG. 1A) was used to locate T-proliferative epitopes. 4 groups of C57B1/6(H-$2^b$) mice were immunised with mixtures of peptides 2Q–5Q (SEQ ID NOS:43, 44, 45, 46), 6Q–9Q (SEQ ID NOS:31, 5, 3, 47), 10Q–12Q (SEQ ID NOS:48, 49, 50) in CFA, or with RPMI in CFA. Pooled LNC from each group were challenged in vitro with 2 or 20 µg/ml of individual peptides and proliferation measured as incorporation of radiolabelled thymidine. The data shown in FIG. 1B are representative of 6 assays. Peptide 8Q (SEQ ID NO:3) consistently elicited strong proliferation in LNC from the 6Q–9Q (SEQ ID NOS:31, 5, 3, 47) immunised group (FIG. 1B.b). Peptide 7Q (SEQ ID NO:5) elicited a weaker response in this group. Peptides 8Q (SEQ ID NO:3) and 7Q (SEQ ID NO:5) share a 12 amino acid overlap at position 44–55. Weak and inconsistent responses were seen in LNC from 2Q–5Q (SEQ ID NOS:43–46) immunised mice, when challenged with peptides 4Q (SEQ ID NO:45) and 5Q (SEQ ID NO:46) (3 out of 6 experiments) FIG. 1B,a). No further peptides from the 2Q–12Q (SEQ ID Nos. 43, 44, 45, 46, 31, 5, 3, 47, 48, 49, 50) series induced proliferation in assays using LNC from appropriately immunised BlO.A(4R)(H-S$^{h2}$), or Balb/c (h-2$^d$) mice (data not shown).

In order to investigate the MHC restriction of the proliferative response to 8Q (SEQ ID NO:3), a series of congenic mice, differing only at the MHC class 2 locus, and other in-bred strains of MHC class 2 haplotype-defined mice, were immunised with mixtures of peptides 8Q (SEQ ID NO:3) and 6Q (SEQ ID NO:31) and their LNC subsequently challenged in vitro with 8Q (SEQ ID No. 3) or 6Q (SEQ ID NO:31) (6Q (SEQ ID NO:31) was included as an internal negative control). Immunised mice from all congenic strains on a B10 (SEQ ID NO:24) background showed strong proliferative responses to peptide 8Q (SEQ ID NO:3), but not to control peptide 6Q (SEQ ID NO:31), over 0.04–27 µg/mol range (FIG. 2a). In further experiments other immunised strains S7R(I-A$^5$I-E$^8$), S94(I-A$^5$I-E$^{kBS}$), C$_3$H(I-A$^k$I-E$^k$), CBA (I-A$^k$I-E$^k$), DBA (I-A$^d$I-E$^d$), Balb/c (I-A$^d$I-E$^d$), C57B1/6(I-A$^b$I-E$^b$) and BL10(I-A$^b$I-E$^b$) all showed proliferative responses to 8Q (SEQ ID NO:3). These data indicate that the proliferative response to peptide 8Q (SEQ ID NO:3) in previously primed mice is not restricted through any of the 5 I-A or 5 I-E alleles tested.

In order to define the minimal peptide which would induce proliferation, LNC from 8Q (SEQ ID NO:3) immunised mice were challenged in vitro with a series of C'-terminal and N'-terminal truncations of 8Q (SEQ ID NO:3) (Table 1). LNC stimulated with peptides B3 (SEQ ID No. 18), B4 (SEQ ID NO:30), 8Q (SEQ ID NO:3), B7 (SEQ ID NO:1), B8 (SEQ ID NO:4), B9 (SEQ ID NO:25) and B10 (SEQ ID NO:24) inclusive showed significant proliferation, indicating that the consensus sequence $^{48}$DRAHYNI$^{54}$ (SEQ ID NO:11) was the minimal proliferative epitope. In a subsequent experiment, LNC from 8Q (SEQ ID NO:3) primed B10.A(2R) and 29R mice proliferated in response to the 7-mer peptide DRAHYNI (SEQ ID NO:11) though the stimulation indices were much lower (6.1 and 5.1 respectively).

The ability of peptide 8Q (SEQ ID NO:3) to prime for a response of LNC to in vitro challenge with HPV16 E7 protein was tested. The proliferation elicited by challenge of LNC from peptide 8Q (SEQ ID NO:3) immunised mice with HPV16 E7 FP and 8Q (SEQ ID NO:3) was of the same order of magnitude, provided challenges were adjusted to be approximately equimolar for 8Q (SEQ ID NO:3) (FIG. 2B).

In an experiment to test whether HPV16 E7 protein would prime for peptide 8Q (SEQ ID NO:3), LNC from mice immunised with HPV16 E7, but not 'sham' immunised mice proliferated when challenged in vitro with 8Q (SEQ ID NO:3) (FIG. 2C).

LNC From Primed Mice Produce Interleukins When Stimulated in Vitro

Supernatant fluid from 8Q (SEQ ID NO:3) and 7Q (SEQ ID NO:5) challenged, but not 6Q (SEQ ID NO:31) or 9Q (SEQ ID NO:47) challenged, LNC from mice previously immunised with a mixture of 6Q–9Q (SEQ ID NOS:31, 5, 3, 47) peptides, induced proliferation of the IL-2/IL-4 dependent cell-line HT-2, (FIG. 2D). Supernatants of LNC from mice immunised, and challenged in vitro, with the other Q-series peptides failed to induce proliferation of HT-2 cells (data not shown).

Having determined that peptide 8Q (SEQ ID NO:3) contained a T-epitope to which primed LNC would respond by proliferation and cytokine production, we then undertook a series of experiments to determine whether primed LNC would provide 'help' to B cells for the production of specific antibody to B cell epitopes of HPV16 E7. Earlier work from our laboratory has defined the location of 3 immunodominant B-cell linear epitopes in the HPV16 E7 protein, recognised by murine monoclonal antibodies (Mabs) (Tindle et al 1990. J. Gen. Virol. 71, 1347–1354). In initial experiments we exploited the fact that peptide 8Q (SEQ ID No. 3), in addition to the T-epitope $^{48}$DRAHYNI$^{54}$ (SEQ ID NO:11) defined above, also contained an immunodominant B-epitope, $^{44}$QAEPD$^{48}$ (SEQ ID NO:12).

Mice Immunised With 8Q (SEQ ID NO:3) Peptide Respond to in Vivo Challenge With Recombinant Vaccinia Virus Containing the HPV16 E7 ORF Gene by Production of Antibody to the E7 Protein The sera of mice immunised with 8Q (SEQ ID NO:3) and infected 3½ weeks later with recombinant vaccinia-E7 virus (VAC-E7), but not wild-type virus (WR-VAC), contained antibodies reactive with 8Q (SEQ ID NO:3) (FIG. 3B) and with HPV16 E7 (FIG. 3A), both of which contain the QAEPD (SEQ ID NO:12) B-epitope.

It is therefore clear that a single immunisation with 8Q (SEQ ID NO:3) peptide primed DRAHYNI (SEQ ID NO:11)-reactive T-helper (Th) cells and also B-cells which recognise the QAEPD (SEQ ID NO:12)-containing peptide for subsequent challenge with whole eukaryotic E7 protein is processed in such a way as to stimulate primed DRAHYNI (SEQ ID NO:11)-reactive Th-cells to provide help for B-cells producing antibody to the QAEPD (SEQ ID NO:12)-containing peptide.

Figure 4A:
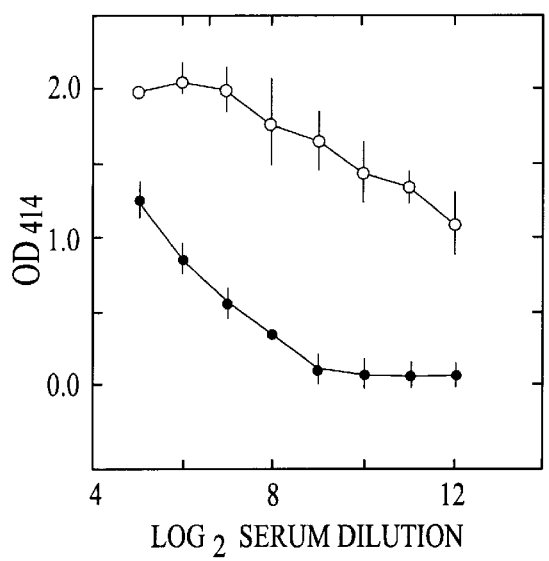
FIG. 4 shows plots of log$_2$ serum dilution versus OD$_{414}$ in four panels, A–D. Sera from B10.A(2R) mice immunised with peptide 8Q (SEQ ID NO:3) or control peptide 3Q (SEQ ID NO:44) in CFA were assayed by ELISA for antibody to peptide 8Q (SEQ ID NO:3, panel A), peptide 7Q (SEQ ID NO:5, panel B), peptide 6Q (SEQ ID NO:31, panel C) and HPV16 E7 FP (panel D).
Figure 4B:
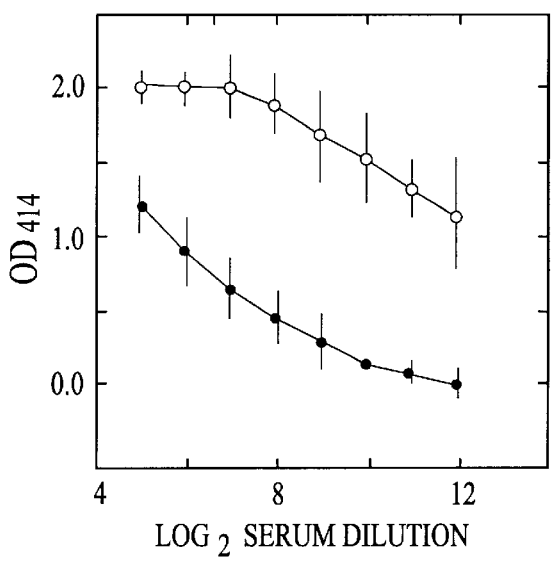
Figure 4C:
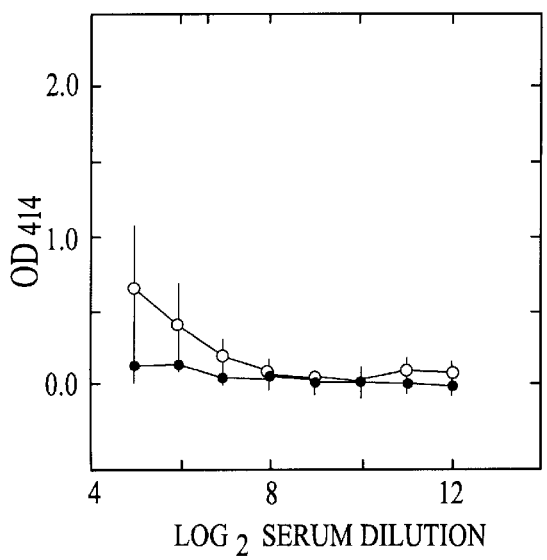
Figure 4D:
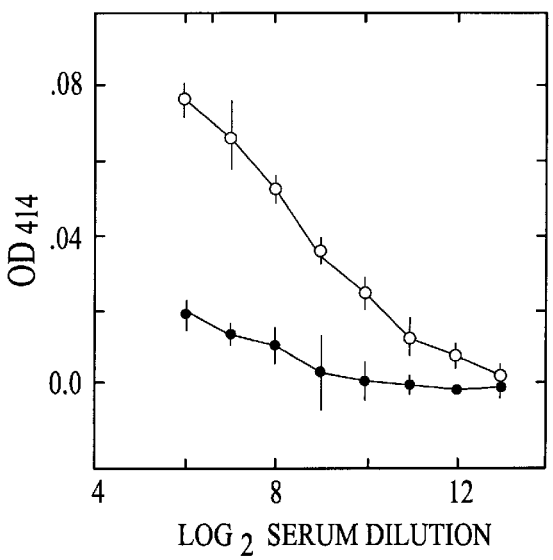

Mice Immunised With Peptides Containing the T-Epitope DRAHYNI (SEQ ID NO:11) and B-Epitope(s) of HPV16 E7 or HPV18 E7 Produce Antibodies Which Specifically Recognise E7 Protein Sera from mice immunised with peptide 8Q (SEQ ID NO:3) reacted in ELISA assay with 8Q (SEQ ID NO:3) and 7Q (SEQ ID NO:5) (FIGS. 4A,B) and HPV16 E7 FP (FIG. 4D) but not control peptides 6Q (SEQ ID NO:31) (FIG. 4C), or 2Q (SEQ ID NO:43), 4Q (SEQ ID NO:45) and 10Q (SEQ ID NO:48) (data not shown). These data suggested that the serum antibodies may have recognised the B-epitope QAEPD (SEQ ID NO:12) contained within 8Q (SEQ ID NO:3), 7Q (SEQ ID NO:5) and HPV16 E7. In a further series of experiments the sera from some mice immunised with peptides B7 or B8 reacted with 8Q (SEQ ID NO:3) and 7Q (SEQ ID NO:5), whereas sera from mice immunised with B16 (SEQ ID NO:22), B17 (SEQ ID NO:23), B19 (SEQ ID NO:11) or B3 (SEQ ID NO:18) did not (Table 2). The data indicated that in order to elicit an antibody response to peptides and HPV16 E7 FP containing the B-epitope QAEPD (SEQ ID NO:12), the immunogen was required to contain the T-epitope DRAHYNI (SEQ ID NO:11) in addition to the sequence QAEPD (SEQ ID NO:12).

Further experiments were carried out to determine if the inclusion of T-epitope DRAHYNI (SEQ ID NO:11) in synthetic peptides used for immunisation would result in help being extended to sequences containing B-epitopes other than QAEPD (SEQ ID NO:12). The sera of 3 mice immunised with peptide B11 (SEQ ID NO:7) all contained antibodies to B-epitopes EYMLD (SEQ ID NO:14) and QAEPD (SEQ ID NO:12), and reacted with HPV16 E7 (Table 2). Reactivity with HPV16 E7 could be absorbed out by pre-incubation of the sera with peptide 8Q (SEQ ID NO:3) (containing QAEPD (SEQ ID NO:12)) and 2Q (SEQ ID NO:43) (containing EYMLD (SEQ ID NO:14)). The serum of one of these mice also contained antibodies to B-epitope IDGP (SEQ ID NO:13). The sera of mice immunised with 7Q (SEQ ID NO:5) contained antibody to QAEPD (SEQ ID NO:12), but not IDGP (SEQ ID NO:13) (Table 2).

In order to determine if the inclusion of DRAHYNI (SEQ ID NO:11) in a synthetic peptide containing a B-epitope from the putative E7 protein of an HPV genotype other than HPV16 could drive the production of heterologous antibody, mice were immunised with peptides GF11 (SEQ ID NO:16), GF12 (SEQ ID NO:33) and GF15 (SEQ ID NO:6) containing an immunodominant linear B-epitope DEIDGVNHQHL (SEQ ID NO:16) of HPV18 E7 (Selvey et al 1990. J. Immunol. 145, 3105–3110). Serum antibodies which recognised a peptide (GF13 (SEQ ID NO:41)) containing the B-epitope, and whole HPV18 E7 were produced in all 3 mice immunised with GF15 (SEQ ID NO:6), which contains intact DRAHYNI (SEQ ID NO:11), but not in mice immunised with GF12 (SEQ ID NO:33) or GF11 (SEQ ID NO:16) where the T-epitope is truncated or absent. GF15 (SEQ ID NO:6) immunised mice simultaneously produced antibody which recognised the HPV16 E7 B-epitope QAEPD (SEQ ID NO:12) and the whole HPV 16 E7 (Table 2).

In mice immunised with synthetic peptides containing both T- and B-epitopes, and which produced antibody, presumably both sets of lymphocytes i.e., The cells and antibody producing B-cells were primed.

Immunisation With T-Epitope Alone can Prime for an Antibody Response

Mice immunised with peptide B3 (SEQ ID NO:18) (containing T-epitope DRAHYNI (SEQ ID NO:11) but no B epitope) and challenged with peptide B7 (SEQ ID NO:1) (containing B-epitope (QAEPD (SEQ ID NO:12) and T-epitope DRAHYNI (SEQ ID NO:11)) produced antibody detectable at 5 days which recognised 8Q (SEQ ID NO:3) and whole HPV16 E7 FP (Table 2). Mice challenged with B3 (SEQ ID NO:18) did not produce antibody. Nor did mice which had been immunised once.

Day Zero Proliferative Assay

PBMC were separated from 60 ml of blood on Ficoll Hypaque and washed three times in RPMI 1640. The cells were counted and diluted to give $10^6$ cells/ml ie. $1.5 \times 10^5$ cells per 150 µl well volume, in complete RPMI 1640 with 10% human pool AB. In this experiment 150 µl of cells at $10^6$ cells/ml were added to the wells of a 96 well U bottomed plate as set out in Table 4. Cells were challenged in triplicate with peptides 101–109 (SEQ ID NOS:34, 35, 36, 37, 9, 10, 38, 39, 40) identified in Table 3. From Table 4 it will be noted that the cells were challenged with 106 alone and other peptides in groups of three at two concentrations with and without PHA. Tetanus toxoid and media alone wells were included as positive and negative controls respectively. The cells were then incubated 7 days at 37° C. with 5% $CO_2$ and labelled overnight with 1 µc/ml $^3$H thymidine. The cells were then harvested, dried and counted and results recorded as counts/minute. The procedure was also modified to challenge cells in quadruplicate and at a peptide concentration of 5 and 15 µg/ml. The results are recorded in Table 5.

Binding of Peptides to ISCOMS

Peptides were synthesized using Fmoc chemistry on an Applied Biosystems 431A peptide synthesiser. Purity of the peptides were checked by HPLC and amino acid analysis and found to be of greater than 90%.

Peptides synthesised:BT5 (A peptide from HPV16 E7 containing the B epitope QAEPD (SEQ ID NO:12) and the T-helper epitope DRAHYNIVTFCCKCD (SEQ ID NO:18)), QAEPDRAHYNIVTFCCKCD (SEQ ID NO:3), LAP20 (the synthetic lipid binding peptide), VSSLLSS-LKEYWSSLKESFS (SEQ ID NO:19), 7Q (a peptide from HPV 16 E7 containing the B epitope QAEPD (SEQ ID NO:12)), EIDGPAGQAEPDRAHYNIVT (SEQ ID NO:5)/, GF110 (a peptide from HIV virus coupled to the HPV16 E7-helper epitope DRAHYNIVTFCCKCD (SEQ ID NO:18)), TRKSIRIQRGPDRAHYNIVTFCCKCD (SEQ ID NO:20).

Coupling of peptides to the lipid binding peptide LAP20 (Pownall et al PNAS 77, 3154–3158, 1980) was performed by the method of Avrameas (7), using glutaraldehyde. Briefly peptides concerned 2 mg were dissolved in 5 ml PBS, 30 µl of a 25% glutaraldehyde solution was added, stirred for 2 hours at room temperature and was kept at 4° C. overnight. Then 1 ml 1M glycine was added and stirred at room temperature for 2 hours and dialysed overnight at 4° C., using dialysis membranes with a molecular weight cutoff of 6000. During the glutaraldehyde treatment stage and during the dialysis stage formation of heavy precipitates were observed with all peptides, except GF23.

Amino acid analysis was performed on BT5, LAP20, and BT5/LAP20 complex to determine the ratio of BT5 to LAP20 in the complex.

Preparation of ISCOMS

The ISCOMS were prepared by the dialysis procedure wherein briefly 2 mg phosphatidyl choline and 1 mg cholesterol was dissolved in a few drops of chloroform and the solvent removed under a stream of nitrogen. The dried lipid mixture was dissolved in 3 ml Tris buffer (20 mM Tris/HCl pH=7.8, 150 mM NaCl containing 1% octylglucoside. 2 mg peptides in 2 ml PBS and 4 ml of a 10% quil-A solution in water was added to the lipid mixture and mixed for 1 hour at room temperature. The mixture was extensively dialysed against PBS overnight at 4° C. The precipitate formed during dialysis was removed by low speed centrifugation. The supernatant was collected and the ISCOMS were separated from free peptide and Quil-A by layering the supernatant on a 10% sucrose in PBS cushion and allowing the ISCOMS to pellet through by centrifugation using a Beckmann TLA 100.3 rotor at 40,000 rpm for 16 hours at 6° C. The ISCOM pellet was dissolved in PBS.

CBA mice 6 to 10 weeks old were used in immunisations. Mice were injected subcutaneously at the base of the tail with 20 µg peptides coupled to ISCOMS, and as a positive control 100 µg peptide in Freund's complete adjuvant. As a negative control 20 ug of BT5/LAP20 in PBS or BT5 with Quil-A and/or lipid was used. After 21 days the mice were bled and boosted with another injection, and after a further 14 days they were bled again. The antibodies were detected by ELISA plates prepared with peptides themselves or recombinant proteins derived from MS2 fusion proteins from E. coli or recombinant baculovirus infected Spodoptera cells. The results of the preparation of the peptide-ISCOM coupling is given in Table 7 and the humoral response to the administration of peptide BT5 in a number of different delivery systems is provided in Table 6.

Monitoring of Peptide Binding to ISCOMS

At each stage of the preparation of ISCOMS, protein assays were performed using BCA protein assay kit (Pierce Chemical Co), and bovine serum albumin was used as the protein standard.

Discussion

In the present study we define a major proliferative T-epitope $^{48}$DRAHYNI$^{54}$ (SEQ ID NO:11) in HPV16 E7, which stimulates the T-cells of all strains of mice of defined haplotype which we have tested. DRAHYNI (SEQ ID NO:11) stimulates cytokine production in responding T cells, and when coupled to a homologous B-epitope and injected into mice, can elicit cognate help for the production of specific antibody which recognises native E7 protein.

As the 2 overlapping peptides 7Q (SEQ ID NO:5) and 8Q (SEQ ID NO:3) stimulated proliferation in primed T cells (FIG. 1), sequences common to both are likely to be responsible. Proliferation experiments with C- and N-terminal truncations of peptide 8Q (SEQ ID NO:3) indicated that the sequence DRAHYNI (SEQ ID NO:11) was the minimal reactive epitope. Our data do not completely exclude the possibility that more than one distinct T cell site may be responsible for proliferation mediated by 7Q (SEQ ID NO:5) and 8Q (SEQ ID NO:3) but we consider it unlikely, since the 7 N-terminal amino acids of 7Q (SEQ ID NO:5) not shared with 8Q (SEQ ID NO:3) are all contained within peptide 6Q (SEQ ID NO:31) which does not contain a proliferative epitope. In many repeated experiments, the proliferative response to 8Q (SEQ ID NO:3) was always an order of magnitude greater than that to 7Q (SEQ ID NO:5) in LNC from appropriately primed mice, suggesting that flanking sequences outside the minimal epitope DRAHYNI (SEQ ID NO:11) could influence response (Rothbard et al. 1988 EMBO Journal 7, 93–100). Further evidence for this supposition was the observation that while challenge of LNC from 8Q (SEQ ID NO:3) primed mice with the 7-mer DRAHYNI (SEQ ID NO:11) induced proliferation, the magnitude of the response was higher when DRAHYNI (SEQ ID NO:11) was presented with C- or N-terminal elongations (Table 1, and text). In some experiments LNC from mice which had not been specifically primed showed low levels of proliferation in response to co-culture with 8Q (SEQ ID NO:3) peptide (FIG. 2A legend). This may be a primary response in vitro and would suggest that the frequency of T-precursors whose TcR recognises DRAHYNI (SEQ ID NO:11) may be high.

It is perhaps surprising that only one major T epitope was identified in the entire HPV16 E7 molecule using the Q-series range of peptides and the 5 MHC haplotypes that were used. Minor proliferation induced by 4Q (SEQ ID NO:45) and 5Q (SEQ ID NO:46) both of which contain algorithm predicted T-sites (FIG. 1) was observed in primed B10A(2R) and C57B1/6 mice although no cytokine production was detectable. The putative T-sequence of 4Q (SEQ ID NO:45) was unable to provide help for antibody production to the adjacent EYMLD (SEQ ID NO:14) B-epitope when peptide 3Q (SEQ ID NO:44), which contains both, was used to immunise mice. Nor could 4Q (SEQ ID NO:45) prime mice for antibody production upon subsequent in vivo challenge with VAC-E7. Although our panel of overlapping peptides was designed to cover the E7 molecule comprehensively, we cannot be entirely certain that other T-cell sites have not been missed, particularly if residues distant from a putative epitopic site can influence T-epitope recognition. DRAHYNI (SEQ ID NO:11) was not predicted by the DeLisi & Berzofsky (1985 PNAS U.S.A. 82, 7048–7072) or Rothbard (above) T-epitope algorithms. The predicted secondary structure of DRAHYNI (SEQ ID NO:11) is a turn or coil at its N-terminal end, while tyrosine and asparagine are likely to form part of a beta-strand extending C" terminally.

We have demonstrated clearly that immunisation of mice with DRAHYNI (SEQ ID NO:11) joined to a B-epitope will elicit antibody reacting specifically with peptides containing the B-epitope and with the whole E7 molecule.

Furthermore, immunising mice with a peptide containing DRAHYNI (SEQ ID NO:11) but no B-epitope elicited a secondary antibody response when mice were subsequently challenged with DRAHYNI (SEQ ID NO:11) plus B-epitope, suggesting that T-activation in the absence of a B cell response is sufficient to prime.

For developing a peptide vaccine, the candidate should have the capability to elicit in vivo a T cell response to the whole native molecule from which the peptide derives. We have shown that a single priming shot of a peptide containing DRAHYNI (SEQ ID NO:11) and the QAEPD (SEQ ID NO:12) B-epitope will induce immunological memory which can be recalled by in vivo subsequent infection with live vaccinia-E7 recombinant virus containing the full length E7 gene. This latter observation indicates that eukaryotic whole E7 may be processed and presented to the immune system in a way that can be seen by antibody secreting B-cells whose functional development has depended on cognate help provided by Th cells stimulated by DRAHYNI (SEQ ID NO:11). The relevance of the anti-peptide response to the recognition of whole eukaryotic E7 protein is further indicated by the observation that murine anti-QAEPD (SEQ ID NO:12) monoclonal antibody recognises native HPV16 E7 in CaSki cells in immunoprecipitation (Tindle et al 1990. Peptide Res. 3, 162–166). In other virus infections the relevance of defined Th and Tc epitopes for anti-viral protection in vivo has been documented for viral proteins which like E7 are not expressed on cell surfaces, e.g. influenza A virus nucleoprotein (Townsend et al 1986 Cell 44, 959–968), cytomegalovirus immediate early protein p89 (del Val et al J. Virol. 62, 3965–3972 1988)), as well as those on the cell surface which probably protect by inducing neutralising antibodies.

The experiments in which mice were immunised with DRAHYNI (SEQ ID NO:11) and B-epitopes linked in various conformations indicated that DRAHYNI (SEQ ID NO:11) could provide cognate help to more than one clone of antibody secreting B cells to produce multiple antibodies of different specificities. It was not the purpose of these experiments to test all permutations, but it was clear that the production of antibody occurred in several combinations of the position and orientation of the B-epitopes with respect to the T-epitope. Similar findings on epitope orientation have been reported by others (Leverly et al Cell Immunol 125, 65–78 (1990)) (Good et al 1987 Science 235, 1059–1062). We have no data to indicate whether DRAHYNI (SEQ ID NO:11) is the T-epitope responsible for providing help for B cells producing anti-QAEPD (SEQ ID NO:12), anti-EYMLD (SEQ ID NO:14) and anti-IDGP (SEQ ID NO:13)

antibody in mice immunized with whole E7/MS2 FP (Tindle et al 1990 Peptide Res. 3, 162–166) where B- and T-epitopes are in their natural configurations as it does in experiments reported here in which the B- and T-epitopes are closely linked. In this context it has been reported that immunodominant Th sites are frequently near the B cell site (Manca et al 1985 Eur. J. Immunol. 15, 345–350).

DRAHYNI (SEQ ID NO:11) fulfils the criteria of an effective T-epitope vaccine for use in out-bred populations, of being recognised in association with many different MHC haplotypes. It joins a small number of stimulating peptides recently described which are recognised in association with multiple MHC haplotypes (Sinigaglia et al 1988) (Milich et al 1988 Proc. Natl. Acad. Sci. U.S.A. 85, 1610–1614), (Nicholas et al 1988 J. Virol. 62, 4465–4473), (Herber-Katz et al 1988 J. Exp. Med. 167, 275–287), (Lai et al 1987 J. Immunol. 139, 3973–3980). While it is believed that requirements for binding to MHC are less stringent than those for binding to TCT (Sette 1987) it is nonetheless surprising that DRAHYNI (SEQ ID NO:11) caused proliferation in, and therefore presumably bound to, all tested Ia haplotypes. It has been suggested that widely reactive peptides are capable of forming a structure closer to an 'ideal' T-epitope that can associate with many class Ia alleles (Shrier et al 1989 J. Immunol. 142, 1166–1176). While introduction of strong heterologous T-epitopes into vaccines has been advocated (eg hepatitis B virus core antigen, (Stahl and Murray 1989 Proc. Natl. Acad. Sci. U.S.A. 86, 6283–6287)) ideally synthetic HPV vaccines would be composed of T and B cells sites derived from the same organism so that latent and/or subsequent infections would elicit a response from both populations of lymphocytes. Such natural boosting is important if constant high levels of antibody are required for protection. A response to an HPV encoded T-epitope is also critical if antibody independent T-cell immunity is required for protection.

Immunisation of mice with whole HPV16 E7 produced as a recombinant fusion protein with MS2 replicase in bacteria, primed for subsequent in vitro challenge with 8Q (SEQ ID NO:3). The magnitude of the response, however, was consistently lower and less reproducible than priming with peptide. Why whole E7 protein primes for 8Q (SEQ ID NO:3) peptide less well than 8Q (SEQ ID NO:3) primes for 8Q (SEQ ID NO:3) was not addressed in this study but presumably relates to processing and presentation of fragments of the priming antigen to the immune system.

A vaccine for prophylactic and therapeutic use to eradicate HPV infection is desirable, since destructive elimination of all virus infection does not appear technically feasible and no specific anti-viral agent is available. 'Attenuated' HPV alone is unlikely to prove successful as a potential vaccine because of its extremely restricted host cell range and its constitutive lack of infectivity. Furthermore, the use of live HPV to vaccinate is out of the question because of the inherent risk that putative HPV oncogenes will integrate into host cell DNA. In any case, this approach is precluded since there is no tissue culture or animal system for producing large amounts of whole HPV. The development of a peptide vaccine requires the delineation of B- and T-epitopes within ORF peptides recognised by the host's immune system, and the interaction between the epitope responsive cells resulting in specific antibody and cytotoxic effectors. Our group has recently defined immunodominant B-epitopes in HPV 16 E7 and HPV18 E7 peptides (Tindle et al 1990 J. Gen. Virol. 71, 1347–1354, Tindle et al 1990 Peptide Res. 3, 162–166, Selvey et al 1990 J. Immunol. 145, 3105–3110).

T-epitope DRAHYNI (SEQ ID NO:11) was identified initially by priming mice in vivo with mixtures of overlapping 11–20 mer peptides spanning the entire putative HPV16 E7 protein as translated from DNA (Seedorf et al 1985) and challenging cells from draining lymph nodes in vitro with individual peptides. Studies with other viruses have shown convincingly that T-epitopes relevant to infection with native virus can be defined by synthetic peptides using a similar strategy (Gao et al 1989 J. Immunol. 143, 3009–3014, Townsend et al 1986 Cell 44, 959–968, Nicholas et al 1989 J. Immunol. 143, 2790–2796, Van de Zee et al 1989).

To the best of our knowledge, the studies reported here describe the first functional T-helper epitope within the ORF proteins of anogenital HPVs. Basic immunological studies such as those reported here and our previous study (Tindle et al Peptide Research 3, 162–166 1990) are required to lay the foundation of an informed vaccine strategy. DRAHYNI (SEQ ID NO:11) is a Th cell stimulating epitope which can be used for eliciting cognate interaction between T- and B-lymphocytes for the production of antibody against whole E7 protein. Using these criteria DRAHYNI (SEQ ID NO:11) is suitable for inclusion into a synthetic subunit vaccine for anogenital HPV.

The experiments discussed above were all applied to mice. It is now evident from other experiments (ie. the DAY ZERO PROLIFERATIVE ASSAY) that have taken place that peptides containing the DRAHYNI (SEQ ID NO:11) T-epitope elicit proliferation in human subjects of haplotypes DR3, DRW8 and DR2, DRW12. The precise restriction element has as yet not been mapped but it is significant that DR2 covers 26% and DR3 covers 21% of the caucasoid population. While in man the epitope therefore shows greater restriction than in mouse it would still seem to be widely applicable.

It will be appreciated from the foregoing that the peptides of the invention can be made synthetically using standard techniques well known to the skilled chemist. However it should be emphasised that the peptides of the invention can also be produced by recombinant DNA methods as will also be known to the skilled addressee.

TABLE 1

MAPPING THE MINIMAL T-PROLOFERATIVE EPITONE IN THE 8Q PEPTIDE OF HPV16 E7
CHALLENGE PEPTIDE

| SEQ ID NO | DESIGNATION | POSITION | SEQUENCE | STIMULATION INDEX[1] |
|---|---|---|---|---|
| 21 | B6 | 44–50 | QAEPDRA | 1.3 |
| 22 | B16 | 44–51 | QAEPDRAH | 1.0 |
| 23 | B17 | 44–52 | QAEPDRAHY | 1.0 |
| 1 | B7 | 44–54 | QAEPDRAHYNI | 18.1 |
| 24 | B10 | 44–56 | QAEPDRAHYNIVT | 23.8 |
| 4 | B8 | 44–47 | QAEPDRAHYNIVTF | 27.4 |
| 25 | B9 | 44–60 | QAEPDRAHYNIVTFCCK | 37.2 |
| 26 | B1 | 54–62 | IVTFCCKCD | 1.7 |
| 27 | B2 | 51–62 | HYNIVTFCCKCD | 2.6 |
| 28 | B14 | 50–62 | AHYNIVTFCCKCD | 0.9 |
| 29 | B15 | 49–62 | RAHYNIVTFCCKCD | 0.7 |
| 18 | B3 | 48–62 | DRAHYNIVTFCCKCD | 29.8 |
| 30 | B4 | 45–62 | AEPDRAHYNIVTFCCKCD | 25.2 |
| 3 | 8Q | 44–62 | QAEPDRAHYNIVTFCCKCD | 31.7 |

TABLE 2

IMMUNISATION WITH PEPTIDES CONTAINING T- and B-EPITOPES ELICITS SPECIFIC ANTIBODY

| | | | NUMBER OF MICE PRODUCING SERUM ANTIBODY[1] | | | | | | |
|---|---|---|---|---|---|---|---|---|---|
| IMMUNISING PEPTIDE | | | TO E7 PEPTIDE | | | | | TO WHOLE E7 | |
| SEQ ID NO | DES-IGNA-TION | SEQUENCE[2] | 8Q and 7Q (QAEPD)[3] | 6Q (IDGP) | 2Q and 3Q (EYMLD) | 12Q (NONE) | GF13[6] (DEIDG VNHOHL) | HPV16[4] E7FP | HPV18 E7FP |
| 3 | 8Q | QAEPDRAHYNIVTFCCKCD | 12/14 | — | — | — | nt | 12/14 | nt |
| 1 | B7 | QAEPDRAHYNI | 2/6 | — | — | — | nt | 2/6 | nt |
| 23 | B17 | QAEPDRAHY | — | — | — | — | nt | — | nt |
| 22 | B16 | QAEPDRAH | — | — | — | — | nt | — | nt |
| 4 | B8 | QAEPDRAHYNIVTF | 1/3 | — | — | — | nt | 1/3 | nt |
| 11 | B19 | DRAHYNI | — | — | — | — | nt | — | nt |
| 18 | B3 | DRAHYNIVTFCCKCD | — | — | — | — | nt | — | nt |
| 18 + 22 | B3 + B16[5] | DRAHYNIVTFCCKCD + QAEPDRAH | | | | | | | |
| 5 | 7Q | EIDGPAGQAEPDRAHYNIVT | 3/3 | — | — | — | nt | 2/3 | nt |
| 31 | 6Q | YEQLNDSSEEEDEIDGPAGQ | — | — | — | — | nt | — | nt |
| 7 | B11 | EYMLDAGIDGPAGQAEPDRAHYNIVTFCCKCD | 3/3 | 1/3 | 3/3 | — | nt | 3/3 | nt |
| 8 | B12 | RAHYNIVTFCCKCDQAEPDAGIDGPAGEYMLD | 1/5 | — | 2/5 | — | nt | 2/5 | nt |
| 32 | B13 | QAEPDAGIDGPAGEYMLD | — | — | — | — | nt | — | nt |
| 6 | G15 | QAEPDRAHYNIDEIDGVNHQHL | 2/3 | nt | — | nt | 3/3 | 2/3 | 3/3 |
| 33 | G12 | AHYNIDEIDGVNHQHL | — | nt | — | nt | — | — | — |
| 16 | G11 | DEIDGVNHQHL | — | nt | — | nt | — | — | — |

[1]Sera from individual mice (at least 3 per group) immunised with the various peptide constructs, were reacted over a range of doubling dilutions 1:64–1:40976 with microtitre plates to which were bound peptides 8Q (SEQ ID No. 3), 7Q (SEQ ID No. 5), 6Q (SEQ ID No. 31), 2Q (SEQ ID No. 43), 3Q (SEQ ID No. 44), 12Q (SEQ ID No. 50) or GE 13 (SEQ ID No. 41), and HPV 16 E7 or HPV18 E7, in ELISA assay.
'—' indicates no antibody detected by $^{OP}414$ readings or >1 and <0.1 respectively at a serum dilution of 1:512 for peptides and by readings of >0.5 and <0.1 respectively at a serum dilution of 1:256 for E7 FP.
[2]Sequences QAEPD (SEQ ID No. 12), IDGP (SEQ ID No. 13) and EYMLD (SEQ ID No. 14) are immunodominant linear B-epitopes in HPV16 E7 proteins (Tindle et al. 1990, J. Gen. Virology, 71, 1347–1354). Sequence DEIDGVNHQHL (SEQ ID No. 16) is an immunodominant B-epitopic region in HPV18 E7 (Selvey et al. 1990 J. Immunol. 145, 3105–3110).
[3]Sequences in parentheses indicate B-epitopes which the peptides contain.
[4]None of the sera reactive with HPV16 E7 FP reacted with HPV16 E6 FP (negative control).
[5]Mice were immunised 2–3x ip with 50 μg peptide B3 (SEQ ID No. 18) in CFA at 2 week intervals followed by a final injection of peptide B16 (SEQ ID No. 22). Sera were prepared 3 and 5 days later.
[6]The full sequence of GF 13 is RAHYNIDEIDGVNHQHL (SEQ ID No. 41).

TABLE 3

STRUCTURE OF PEPTIDES GF101-GF109

| SEQ ID NO. | | | NET CHARGE |
|---|---|---|---|
| 34 | GF101 MHGDTPTLHEYMLDLQPE γ | 18AA | 2− |
| 35 | GF102 HEYMLLLQPETTDLYCYE γ γ | 18AA | 4− |
| 36 | GF103 PETTDLYCYEQLNDSSEEEDE γ b | 21AA | 9− |
| 37 | GF104 YEQLNDSSEEEDEIDGPAG b | 19AA | 8− |
| 9 | GF105 EIDGPAGQAEPDRAHYNI | 18AA | 2− |
| 10 | GF106 GQAEPDRAHYNIVTFCCKCD | 20AA | 0 |
| 38 | GF107 IVTFCCKCDSTLRLCVQST | 19AA | 1+ |
| 39 | GF108 DSTLRLCVQSTHVDIRTLE | 19AA | 0 |
| 40 | GF109 THVDIRTLEDLLMGTLGIVCPICSQK | 26AA | 0 |

TABLE 4

CONCENTRATIONS

| Cells challenged with | | | | |
|---|---|---|---|---|
| 106/8Q Controls | 2 μg/ml Tet Tox positive | 20 μg/ml Media negative | 20 μg/ml + PHA media negative | PHA alone |
| 101–103 | 2 μg/ml | 20 μg/ml | 20 μg/ml + PHA | |
| 104–106 | " | " | " | |
| 107–109 | " | " | " | |

TABLE 5

STIMULATION INDICED PRODUCED BY CELLS REPEATEDLY STIMULATED WITH VARIOUS PEPTIDE COMBINATIONS

| Subject | | Peptide Groups 101–103 | 104–106 | 107–109 | 106 | Control Positive Final Stimulation with PHA |
|---|---|---|---|---|---|---|
| NOELA | DAY | | | | | |
| | 0 | 4.8 | 4.1 | — | — | 11.0 |
| DR3 | 20 | — | — | — | — | 252.1 |
| DR11 | 27 | — | — | — | — | 67.5 |
| IAN | DAY | | | | | |
| DR4 | 0 | 3.6 | 3.7 | — | — | 62.2 |
| DR7 | 20 | — | — | — | — | 180.2 |
| | 27 | — | — | — | — | 10.4 |
| JOE | DAY | | | | | |
| | 0 | — | 2.1 | — | 2.1 | 2.0 |
| DR2 | 20 | 3.13 | 8.1 | 556.2 | — | 251.6 |
| DRW12 | 27 | — | — | — | — | 475.7 |
| JULIA | DAY | | | | | |
| | 0 | 2.9 | — | — | — | 1.94 |
| DR1 | 20 | — | — | 2.26 | — | 229.3 |
| DR4 | 27 | 2.2 | — | 10.6 | — | 193.1 |
| CHEONG | | | | | | |
| | 0 | 2.1 | — | — | — | 32.5 |
| DR2 | 20 | — | — | — | — | 671.9 |
| DRW9 | NA | — | — | — | — | 165.9 |
| DAVIDSON | | | | | | |
| | 0 | 5.9/4.4** | 7.1/5.3 | 4.3/2.8 | 2.8/2.4 | 20.9 |
| DR3 | 20 | 9.2 | — | — | 2.6*** | 31.4 |
| DRW8 | NA | 2.0 | — | — | — | 4.3 |
| TREVOR | | | | | | |
| | 0 | — | — | 19.9 | — | 222.8 |
| DR4 | 20 | — | — | — | — | — |
| DRW6 | 27 | — | — | — | — | — |
| BRAD | | | | | | |
| | 0 | — | — | — | — | 151.8 |
| DR3 | 20 | — | — | — | — | — |
| DRW6 | 27 | — | — | — | — | — |

TABLE 6

Influence of the antigen delivery system on the humoral immune response to the peptide BT5

| Delivery system* | Antigen# | μg peptide | Number of mice with measurable antibody to | | |
|---|---|---|---|---|---|
| | | | 7Q | 16E7/MS2 | 18E7/MS2 |
| CFA | BT5 | 100 | 2/2 | 2/2 | 0/2 |
| ISCOM | BT5/LAP20 | 20 | 2/3 | 2/3 | 0/3 |
| ISCOM | BT5 | 20 | 0/2 | 0/2 | 0/2 |
| Saline | BT5/LAP20 | 20 | 0/4 | ND | ND |

*Mice immunized on day 0 and day 21, and bled on day 35
See methods
No antibodies were detected in the first bleed which was done on day 21.

TABLE 7

| Total protein at each step | Peptide used which is treated with glutaraldehyde | | | |
|---|---|---|---|---|
| | BT5/LAP20 | BT5 | GF23/LAP20 | GF23 |
| 1). After glutaraldehyde treatment and dialysis | 600 μg | 600 μg | 125 μg | 125 μg |
| 2). After ISCOM prep. and dialysis, and removal of the precipitate | 334 μg | 145 μg | 56 μg (164 ug) | 36 μg (153 μg) |
| 3). After ultracentifugation to remove unbound peptide from ISCOMs | 15.6 μg | 9.9 μg | 15 μg | 16 μg |

Legend
FIG. 1

A. The set of overlapping peptides (termed 2Q–12Q (SEQ ID NOS:43, 44, 45, 46, 31, 5, 3, 47, 48, 49, 50)) spanning the putative HPV16 E7 protein, used to locate the position of T-proliferative epitopes (see text). Linear B-epitopes defined by monoclonal antibodies 8F, 4F and 10F (Tindle et al 1990) are boxed. Underlining denotes the positions of putative T-epitopes as predicted by Rothbard (r) and DeLisi & Berzofsky (b) algorithms respectively.

B. Lymph Node Cell (LNC) proliferation assay. LNC from C57B1/6 mice immunised with equimolar mixes in CFA of (panel a) peptides 2Q–5Q (SEQ ID NOS:43, 44, 45, 46) inclusive, (panel b) peptides 6Q–9Q (SEQ ID NOS:31, 5, 3, 47) inclusive and (panel c) peptides 10Q–12Q (SEQ ID NOS:48, 49, 50) inclusive (3 mice per group, cells pooled) were challenged in vitro with 20 μg/ml or 2 μg/ml of individual peptides 2Q–12Q (SEQ ID NOS:43, 44, 45, 46, 31, 5, 3, 47, 48, 49, 50). Background (no added Antigen) was 845±90 cpm for 2Q–5Q (SEQ ID NOS:43, 44, 45, 46) immunised mice, 1277±330 cpm for 6Q–9Q (SEQ ID NOS:31, 5, 3, 47) mice, and 1190±312 for 10Q–12Q (SEQ ID NOS:48, 49, 50) mice, and was subtracted from the results with peptide. Results are shown as arithmetic mean of triplicate wells. A positive control of PPD challenged LNC gave 168, 849±8,346 cpm.

Legend
FIG. 2

The in vitro proliferative response (panels A–C) and lymphokine production (panel D) of LNC from mice immunised 8 days previously with HPV16 E7 or E7 peptides, and challenged with HPV16 E7 or various E7 peptides.

A. LNC from congenic mice (3 mice per group, cells pooled) immunised with an equimolar mix of peptides 8Q (SEQ ID NO:3) and 6Q (SEQ ID NO:31) were challenged with various concentrations of 8Q (SEQ ID NO:3) (open symbols) or 6Q (SEQ ID NO:31) (closed symbols). B10.D2 (I-A$^{dI-E}$d); B10.A (I-A$^a$I-E$^a$); B10.BR (I-A$^k$I-E$^k$); B10.A (2R) (I-A$^k$I-E$^d$); B10.A (4R) (I-A$^k$I-E$^b$). Background cpm (no added antigen) and PPD response were 2,638 and 88,105 for B10.D2; 7,854 and 75,061 for B10.A; 2.600 and 93,503 for B10.BR; 1,091 and 88,721 for B10.A (2R); and 2,600 and 93,376 for B10.A(4R). No response to peptide 8Q (SEQ ID NO:3) was seen in 'sham'-immunised mice (RPMI plus adjuvant) except in B10.A and B10.A9 (2R) mice which recorded 15,437 and 18,972 cpm and 5,623 and 8,747 cpm at 8Q (SEQ ID NO:3) peptide concentrations of 9 and 27 μg/ml respectively.

B. LNC from 8Q (SEQ ID No. 3) or 'sham'-immunised B10A(2R) mice (5 per group) were challenged with 16 or 64 μg/ml of HPV16 E7 FP, or 2 or 8 μg/ml of 8Q (SEQ ID NO:3). The HPV16 E7 and 8Q (SEQ ID NO:3) challenge doses were approximately equimolar for the 8Q (SEQ ID NO:3) sequence. Background controls (no added antigen) and PPD controls were 1269 cpm and 98,775 cpm respectively.

C. B10.A (2R) mice were immunised with 100 μg HPV16 E7 FP or RPMI ('sham') (5 mice per group) and LNC were challenged with 0.1, 1.0 and 10 μg/ml of 8Q (SEQ ID NO:3). Background controls (no added antigen) and PPD controls were 361 cpm. and 68,872 cpm. respectively for HPV16 E7 FP immunised mice.

D. 4 Groups of 3 B10.A(4R) mice were immunised with 50 μg of equimolar mixtures of peptides 2Q–5Q (SEQ ID NOS:43, 44, 45, 46) inc., 6Q–9Q (SEQ ID NOS:31, 5, 3, 47) inc., 10Q–12Q SEQ ID NOS:48, 49, 50) inc. or PBS in CFA ('sham'). LNC from each group were pooled and challenged with each of the peptides at 67 and 6.7 μg/ml individually in separate wells (3 wells per concentration per peptide). Culture supernatants were harvested 3 days later and added at 1:2 dilution to HT-2 cells. The HT-2 cells were pulsed 42–44 h. later for 6 h. with $^3$H-thymidine, harvested and counted. For clarity, only data on LNC from mice primed with peptide mixture 6Q–9Q (SEQ ID NOS:31, 5, 3, 47) and challenged with 6Q (SEQ ID NO:31), 7Q (SEQ ID NO:5), 8Q (SEQ ID NO:3) and 9Q (SEQ ID NO:47) are shown. (Data not shown: Supernatants of LNCs from mice primed with 2Q–5Q (SEQ ID NOS:43, 44, 45, 46), 10Q–12Q (SEQ ID NOS:48, 49, 50) or PBS and challenged with each of the peptides individually failed to stimulate HT-2 cell division). Background, with RPMI added to HT-2 cells in place of supernatants was 1,870±720 cpm.

Legend
FIG. 3

Immunisation with peptide 8Q (SEQ ID NO:3) primed mice for in vivo challenge with HPV16 E7 produced from a recombinant vaccinia virus.

Five groups of 6 mice were immunised with 50–100 μg of equimolar mixtures of peptides 2Q–5Q (SEQ ID NOS:43, 44, 45, 46) inc., 6Q–9Q (SEQ ID NOS:31, 5, 3, 47) inc., 10Q–12Q (SEQ ID NOS:48, 49, 50) inc., or 8Q (SEQ ID NO:3) alone, or PBS in CFA ('sham'). 3½ weeks later, each group was divided; 3 mice were challenged with VAC-E7, the other 3 with WR-VAC. Sera were collected after a further 8 and 13 days, and antibody to HPV16.E7 FP and peptides 8Q (SEQ ID NO:3) (containing QAEPD (SEQ ID NO:12) B-epitope), 2Q (SEQ ID NO:43) (containing EYMLD (SEQ ID NO:14) B-epitope), 6Q (SEQ ID NO:31) (containing IDGP (SEQ ID NO:13) B-epitope) or 12Q (SEQ ID No. 50) (containing no B-epitope) was assessed by ELISA. For clarity, only ELISA results on pooled 8 day sera from 8Q (SEQ ID NO:3) primed mice (○,●) and 'sham' primed mice (▽,▼) challenged with VAC-E7 (○,●), or WR-VAC (○,▼), on HPV16 E7 fusion protein (A), or peptide 8Q (SEQ ID NO:3) are shown. (Data not shown: Sera from 8Q (SEQ ID NO:3) primed mice challenged with VAC E7 or WR-VAC did not react with 2Q (SEQ ID NO:43), 6Q (SEQ ID NO:31) or 12Q (SEQ ID NO:50) peptides. Sera from mice primed with 2Q–5Q (SEQ ID NOS:43, 44, 45, 46), or 10–12Q (SEQ ID NOS:48, 49, 50) and challenged with VAC E7 or WR-VAC did not react with peptides 2Q (SEQ ID NO:43), 6Q (SEQ ID NO:31), 8Q (SEQ ID NO:3) or 12Q (SEQ ID NO:50) or with HPV16 E7 FP. Sera from mice immunised with 6Q–9Q (SEQ ID NOS:31, 5, 3, 47) and infected with VAC-E7 or WR-VAC showed a reactivity pattern identical to mice immunised with 8Q (SEQ ID NO:3) alone. Results on 13 day sera were similar to those shown for 8 day sera).

Legend

FIG. 4

Sera from B10.A (2R) mice immunised with peptide 8Q (SEQ ID NO:3) (○) or control peptide 3Q (SEQ ID NO:44) (●) in CFA were assayed by ELISA for antibody to (panel A) peptide 8Q (SEQ ID NO:3), (panel B) peptide 7Q (SEQ ID NO:5), (panel C) peptide 6Q (SEQ ID NO:5), (panel D) HPV16 E7 FP. Data points are arithmetic means (±standard deviation) of sera collected individually from 3 mice. (Data not shown: For panels A–C further negative controls were 1) lack of reactivity of sera from mice immunised with 2Q (SEQ ID NO:43), 4Q (SEQ ID NO:45), 10Q (SEQ ID NO:48) and PBS on plates coated with 8Q (SEQ ID NO:3) and 7Q (SEQ ID NO:5). 2) the lack of reactivity of sera from mice immunised with 8Q (SEQ ID NO:3) on plates coated with peptides 2Q (SEQ ID NO:43), 4Q (SEQ ID NO:45) and 10Q (SEQ ID NO:48). For panel D, a further negative control was the lack of reactivity of sera from mice immunised with 8Q (SEQ ID NO:3) on plates coated with HPV16 E6 FP).

Legend

Table 1

1. Lymph node cells from B10.A(2R) mice immunised with peptide 8Q (SEQ ID NO:3) (3 mice, cells pooled) were challenged in vitro with peptides as indicated. The cells were cultured for 4 days and proliferation measured by [$^3$H]-thymidine incorporation. The data in this table were pooled from 4 experiments and proliferation is expressed as a stimulation index to normalise for inter-experimental variation. The stimulation index was defined as the ratio of mean cpm of test wells with added antigen, to the mean cpm of test wells with no added antigen. Background cpm (no added antigen) was within the range 3807–5423.

What is claimed is:

1. A pharmaceutical composition comprising (i) a pharmaceutically acceptable adjuvant and (ii) an immunogenic peptide comprising (a) a T epitope which comprises the amino acid sequence DRAHYNI (SEQ ID NO: 11) and (b) one or more B epitopes of HPV 16 E7 protein or HPV 18 E7 protein, wherein the immunogenic peptide does not comprise the full-length HPV 16 E7 protein or the full-length HPV 18 E7 protein, and wherein the composition in use elicits a strong antibody response to challenge by at least one of the HPV 16 E7 protein and the HPV 18 E7 protein.

2. A pharmaceutical composition according to claim 1, wherein the B epitopes from HPV16 E7 ORF are selected from the group consisting of QAEPD (SEQ ID NO:12), IDGP (SEQ ID NO:13), EYMLD (SEQ ID NO:14) and YMLD (SEQ ID NO:15).

3. A pharmaceutical composition according to claim 1, wherein the B epitopes from HPV18 E7 ORF are selected from the group consisting of DEIDGVNHQHL (SEQ ID NO:16) and SEENED (SEQ ID NO:17).

4. A pharmaceutical composition according to claim 1, wherein the peptide has the sequence QAEPDRAHYNIVTFCCKCD (SEQ ID NO:3).

5. A pharmaceutical composition according to claim 1, wherein the peptide has the sequence QAEPDRAHYNI (SEQ ID NO:1).

6. A pharmaceutical composition according to claim 1, wherein the peptide has the sequence QAEPDRAHYNIVTF (SEQ ID NO:4).

7. A pharmaceutical composition according to claim 1, wherein the peptide has the sequence EIDGPAGQAEPDRAHYNIVT (SEQ ID NO:5).

8. A pharmaceutical composition according to claim 1, wherein the peptide has the sequence QAEPDRAHYNIDEIDGVNHQHL (SEQ ID NO:6).

9. A pharmaceutical composition according to claim 1, wherein the peptide has the sequence EYMLDAGIDGPAGQAEPDRAHYNIVTFCCKCD (SEQ ID NO:7).

10. A pharmaceutical composition according to claim 1, wherein the peptide has the sequence EIDGPAGQAEPDRAHYNI (SEQ ID NO:9).

11. A pharmaceutical composition according to claim 1, wherein the peptide has the sequence GQAEPDRAHYNIVTFCCKCD (SEQ ID NO:10).

12. A pharmaceutical composition according to claim 1, further including as an adjuvant ISCOMS which are chemically bound to the peptide.

13. A pharmaceutical composition comprising (i) a pharmaceutically acceptable adjuvant and (ii) an immunogenic peptide comprising (a) a T epitope which comprises the amino acid sequence DRAHYNI (SEQ ID NO:11) and (b) at least one B epitopes of HPV 16 E7 protein or HPV 18 E7 protein, the B epitopes selected from the group consisting of QAEPD (SEQ ID NO: 12), IDGP (SEQ ID NO: 13), EYMLD (SEQ ID NO:14), YMLD (SEQ ID NO: 15), DEIDGVNHQHL (SEQ ID NO: 16) AND SEENED (SEQ ID NO: 17) wherein the immunogenic peptide does not comprise the full-length HPV 16 E7 protein or the full-length HPV 18 E7 protein.

14. A peptide consisting of the sequence QAEPDRAHYNIVTFCCKCD (SEQ ID NO:3).

15. A peptide consisting of the sequence QAEPDRAHYNI (SEQ ID NO:1).

16. A peptide consisting of the sequence QAEPDRAHYNIVTF (SEQ ID NO:4).

17. A peptide consisting of the sequence EIDGPAGQAEPDRAHYNIVT (SEQ ID NO:5).

18. A peptide consisting of the sequence QAEPDRAHYNIDEIDGVNHQHL (SEQ ID NO:6).

19. A peptide consisting of the sequence EYMLDAGIDGPAGQAEPDRAHYNIVTFCCKCD (SEQ ID NO:7).

20. A peptide consisting of the sequence RAHYNIVTFCCKCDQAEPDAGIDGPAGEYMLD (SEQ ID NO:8).

21. A peptide consisting of the sequence EIDGPAGQAEPDRAHYNI (SEQ ID NO:9).

22. A peptide consisting of the sequence GQAEPDRAHYNIVTFCCKCD (SEQ ID NO:10).

23. A method of immunizing a mammal against HPV 16 or HPV 18 infection, the method including the step of administering an amount of the pharmaceutical composition of claim 1 sufficient to induce immunological memory in the mammal.

* * * * *